(12) United States Patent
Flynn et al.

(10) Patent No.: US 8,466,163 B2
(45) Date of Patent: Jun. 18, 2013

(54) FURO[2,3-D]PYRIMIDINES AND RELATED COMPOUNDS AND METHODS FOR TREATING DISEASE STATES BY INHIBITING TUBULIN POLYMERIZATION

(75) Inventors: Bernard Luke Flynn, Vermont (AU); Jason Hugh Chaplin, Thornbury (AU); Dharam Paul, Bellfield (AU); Damian Wojciech Grobelny, Watsonia North (AU); Brian Kelly, Ringwood East (AU)

(73) Assignee: Bionomics Limited, Thebarton (AU)

( * ) Notice: Subject to any disclaimer, the term of this patent is extended or adjusted under 35 U.S.C. 154(b) by 927 days.

(21) Appl. No.: 12/448,146

(22) PCT Filed: Dec. 11, 2007

(86) PCT No.: PCT/AU2007/001908
§ 371 (c)(1),
(2), (4) Date: Oct. 13, 2009

(87) PCT Pub. No.: WO2008/070908
PCT Pub. Date: Jun. 19, 2008

(65) Prior Publication Data
US 2010/0048591 A1  Feb. 25, 2010

Related U.S. Application Data

(60) Provisional application No. 60/874,125, filed on Dec. 11, 2006.

(51) Int. Cl.
*A61K 31/519* (2006.01)
*A61P 35/00* (2006.01)

(52) U.S. Cl.
USPC ........ 514/260.1; 544/278; 544/350; 514/249; 514/302; 546/115; 546/116

(58) Field of Classification Search
USPC ....................................... 544/278; 514/260.1
See application file for complete search history.

(56) References Cited

U.S. PATENT DOCUMENTS

2005/0004142 A1 * 1/2005 Adams et al. ............... 514/260.1
2006/0040961 A1 * 2/2006 Buchanan et al. ......... 514/260.1
2006/0148801 A1   7/2006 Hsieh et al.

FOREIGN PATENT DOCUMENTS

WO  WO 02/060872 A1  8/2002
WO  WO 03/022852 A2  3/2003
WO  WO 03/070241 A1  8/2003

OTHER PUBLICATIONS

Dorwald, F. A. Side Reactions in Organic Synthesis, 2005, Wiley: VCH, Weinheim p. IX of Preface.*
International Search Report from PCT Application PCT/US2007/001908 dated Feb. 8, 2008.
Arya, V. et al. "Synthesis of New Heterocycles: Part V—Synthesis of Thieno[2,3-*d*]pyrimidines & Certain Related Condensed Thiophenes" Indian Journal of Chemistry, vol. 9, Nov. 1971, pp. 1209-1212.
Collini, M. et al. "The Solid Phase Synthesis of Tri-Substituted Indoles" Tetrahedron Letters, vol. 38, No. 46, pp. 7963-7966 (1997).
Flynn, B. et al. A Novel Palladium-Mediated Coupling Approach to 2,3-Disubstituted Benzo[*b*]thiophenes and Its Application to the Synthesis of Tubulin Binding Agents: Organic Letters 2001, vol. 3, No. 5, 651-654.
Han, Y. et al. "Solid Phase Parallel Synthesis of Highly Substituted Thiophene Derivatives and Identification of Novel Phosphodiesterase-4 (PDE-4) Inhibitors" Tetrahedron 55 (1999) 11669-11685.
Johnson, M. et al. "Solid Phase Chemistry Approach to the SAR Development of a Novel Class of Active Site-Directed Thrombin Inhibitors" Tetrahedron 55 (1999) 11641-11652.
Pettit, G. et al. "Antineoplastic Agents 322. Synthesis of Combretastatin A-4 Prodrugs" Anti-Cancer Drug Design (1995) 10, 299-309.
Wahid, F. et al. "Synthesis and Biological Evaluation of 5-Arylfuro[2,3-*d*]pyrimidines as Novel Dihydrofolate Reductase Inhibitors" Chem. Pharm. Bull. 47(2) 156-164 (1999).

* cited by examiner

*Primary Examiner* — Susanna Moore
(74) *Attorney, Agent, or Firm* — Wolf, Greenfield & Sacks, P.C.; C. Hunter Baker; Emilie Porter Huck

(57) ABSTRACT

The present invention relates generally to chemical compounds and methods for their use and preparation. In particular, the invention relates to chemical compounds which may possess useful therapeutic activity, use of these compounds in methods of therapy and the manufacture of medicaments as well as compositions containing these compounds.

16 Claims, No Drawings

FURO[2,3-D]PYRIMIDINES AND RELATED COMPOUNDS AND METHODS FOR TREATING DISEASE STATES BY INHIBITING TUBULIN POLYMERIZATION

CROSS-REFERENCE TO RELATED APPLICATIONS

The present application is a national stage filing under 35 U.S.C. §371 of international PCT application, PCT/AU2007/001908, filed Dec. 11, 2007, which claims priority under 35 U.S.C. §119(e) to U.S. provisional patent application, U.S. Ser. No. 60/874,125, filed Dec. 11, 2006, each of which is incorporated herein by reference.

FIELD OF THE INVENTION

The present invention relates generally to chemical compounds and methods for their use and preparation. In particular, the invention relates to chemical compounds which may possess useful therapeutic activity, use of these compounds in methods of therapy and the manufacture of medicaments as well as compositions containing these compounds.

BACKGROUND OF THE INVENTION

Tubulin is an important target in controlling disease states associated with cell proliferation such as cancer and inflammation (eg, psoriasis). Tubulin is composed of a heterodimer of two related proteins called α and β tubulin. Tubulin polymerises to form structures called microtubules. Compounds that inhibit tubulin's ability to polymerise to form microtubules interrupt cell division which is dependent on the formation of microtubules to form mitotic spindles. Examples of such compounds include the Vinca alkaloids such as vincristine and vinblastine.

Furthermore, compounds that inhibit the depolymerisation of microtubules can also prevent cell division since they often disrupt the proper formation of mitotic spindles which must also disassemble in order for cell division to be completed. Interruption of the mitotic process in this manner often induces cell death by an apoptotic mechanism. Examples of compounds which act in this manner include the taxoids such as paclitaxel.

For these antimitotic agents, selectivity for diseased versus non-diseased tissue is based on relative rates of proliferation, where the diseased tissue more rapidly proliferates. Accordingly, diseased tissue is generally more sensitive to the effect of these agents because it is more likely to be in a state of mitosis which is the stage of a cell's life cycle affected by agents that target tubulin. Unfortunately however, a number of normal, healthy tissues also have quite high rates of proliferation (for example hair follicles and the lining of the gastro-intestinal tract) and accordingly, these tissues can be damaged during chemotherapy with these agents.

Tubulin is also a target for treating disease states that are dependent or result from the abnormal formation of blood vessels (neovascularisation) such as in cancerous tumours and in ocular myopathy. In these cases the cytoskeleton of the vascular endothelial cells are disrupted through depolymerisation of microtubles, which results from inhibiting the polymerisation of tubulin to form microtubules. Microtubule length is dependent on the rate of depolymerisation versus polymerisation. Depolymerising microtubules through inhibition of polymerisation leads to a change in endothelial cell morphology, which then causes a blockage or shutdown in blood flow. In the case of cancerous tumours, blood flow to the diseased tissue is stopped, depriving the tumour of oxygen and nutrients leading to necrotic cell death. Neovascular systems are more sensitive to these agents because they are more dependent on microtubule cytoskeletons than normal, healthy, vascular endothelial cells which are also supported by actin based cytoskeletal structures. For a number of tubulin polymerisation inhibitors (TPIs) that target the colchicine binding site of tubulin, the vascular targeting modality can be achieved at a lower in vivo concentration than the antiproliferative modality. In theory though, agents that target the colchicine binding domain of tubulin are potentially dual mode agents (ie. antimitotic and antivascular).

One of the most potent inhibitors of tubulin polymerisation that binds to the colchicine binding domain of tubulin is the cis-stilbene, combretastatin A4 (CA4) (1). Due to its insolubility CA4 is administered as its prodrug equivalent combretastatin A4 disodium phosphate (CA4P) (2), where the phosphate is rapidly cleaved in vivo. CA4P is currently undergoing phase I and II clinical trials and is the most advanced vascular targeting agent being trialed. In view of some of the draw-backs associated with CA4P, such as, instability (can isomerise to the inactive trans-stilbene), toxicity and rapid clearance, a number of synthetic groups have sought to prepare more stable analogues that could be designed to exhibit an improved therapeutic index and exhibit improved pharmacokinetics. Recently, a number of TPIs have been identified that contain the benzofuran, indole or benzothiophene ring systems (3). Such ring systems are quite stable and should over come the stability issues associated with CA4P. Unfortunately, such compounds only exhibit moderate tubulin binding and anti-mitotic activity. Accordingly, there exists a need to identify other compounds which are more stable than CA4 and exhibit satisfactory pharmacological properties and/or activity.

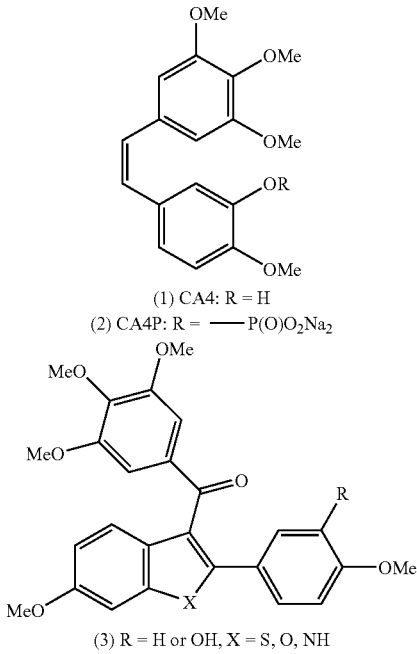

(1) CA4: R = H
(2) CA4P: R = ——P(O)O₂Na₂

(3) R = H or OH, X = S, O, NH

SUMMARY OF THE INVENTION

The present invention provides compounds of formula (I) and salts thereof;

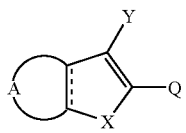

wherein;
X represents O, S, SO, SO$_2$, Se, SeO, or SeO$_2$;
A together with the atoms to which it is attached forms an optionally substituted heteroaryl or optionally substituted heterocyclyl group;
=== represents an optional double bond;
Y represents a group of formula (i) or (ii);

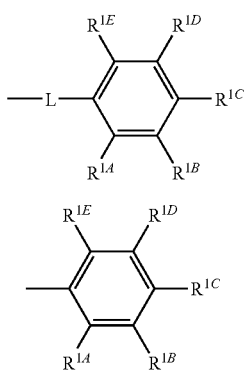

wherein each R$^{1A}$-R$^{1D}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of R$^{1A}$ and R$^{1B}$, R$^{1B}$ and R$^{1C}$, R$^{1C}$ and R$^{1D}$, and R$^{1D}$ and R$^{1E}$, together form an optionally substituted aryl, optionally substituted heterocyclyl, optionally substituted heteroaryl, optionally substituted cycloalkyl, or optionally substituted cycloalkenyl;
L represents C=O, O, S, SO, SO$_2$, Se, SeO, SeO$_2$, C=NZ', or NR' where Z' is H, optionally substituted alkyl, optionally substituted aryl or optionally substituted amino, and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl; and Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl; and wherein Y and Q do not represent the same group.

The present invention also provides a method for treating a disease state by inhibiting tubulin polymerisation including the step of administering to a patient in need thereof a compound of formula (II) or a pharmaceutically acceptable salt thereof;

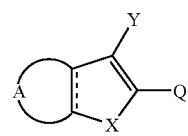

wherein;
X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;
A together with the atoms to which it is attached forms an optionally substituted heteroaryl or optionally substituted heterocyclyl group;
=== represents an optional double bond;
Y represents a group of formula (i) or (ii);

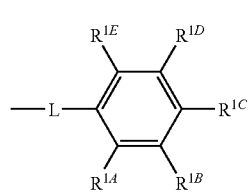

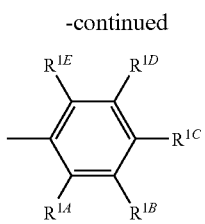

wherein each $R^{1A}$-$R^{1D}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{1A}$ and $R^{1B}$, $R^{1B}$ and $R^{1C}$, $R^{1C}$ and $R^{1D}$, and $R^{1D}$ and $R^{1E}$, together form an optionally substituted aryl, optionally substituted heterocyclyl, optionally substituted heteroaryl, optionally substituted cycloalkyl, or optionally substituted cycloalkenyl;

L represents C=O, O, S, SO, $SO_2$, Se, SeO, $SeO_2$, C=NZ', or NR' where Z' is H, optionally substituted alkyl, optionally substituted aryl or optionally substituted amino, and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl; and Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'"R'", where each R'" independently represents H, optionally substituted alkyl, optionally substituted alkenyl, optionally substituted alkynyl, optionally substituted aryl and optionally substituted heteroaryl.

The present invention also provides the use of a compound of formula (II) or a salt thereof:

wherein;
X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

A together with the atoms to which it is attached forms an optionally substituted heteroaryl or optionally substituted heterocyclyl group;

≡≡≡ represents an optional double bond;
Y represents a group of formula (i) or (ii);

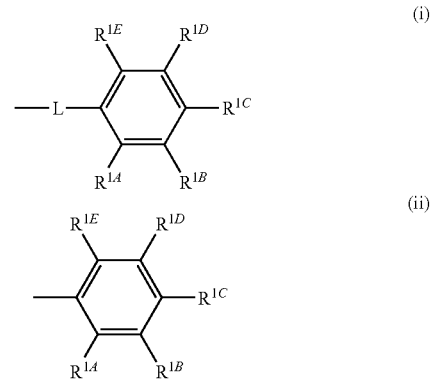

wherein each $R^{1A}$-$R^{1D}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{1A}$ and $R^{1B}$, $R^{1B}$ and $R^{1C}$, $R^{1C}$ and $R^{1D}$, and $R^{1D}$ and $R^{1E}$, together form an optionally substituted aryl, optionally substituted heterocyclyl, optionally substituted heteroaryl, optionally substituted cycloalkyl, or optionally substituted cycloalkenyl;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl; and Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR", SR" or NR"R", where each R' independently represents, H, optionally substituted alkyl, optionally substituted alkenyl, optionally substituted alknyl, optionally substituted heterocyclyl, optionally substituted aryl, optionally substituted heteroaryl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl, in the manufacture of a medicament for the treatment of a disease state by inhibiting tubulin polymerisation.

DESCRIPTION OF THE PREFERRED EMBODIMENTS

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like. Especially preferred are "lower alkyl" groups which have 1 to 4 carbon atoms.

"Alkylene" refers to divalent alkyl groups preferably having from 1 to 10 carbon atoms and more preferably 1 to 6 carbon atoms. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

"Aryl" refers to an unsaturated aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=$CH_2$), n-propenyl (—$CH_2$CH=$CH_2$), iso-propenyl (—C($CH_3$)=$CH_2$), but-2-enyl (—$CH_2$CH=$CHCH_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (—CH=CH—), and the propenylene isomers (e.g., —$CH_2$CH=CH— and —C($CH_3$)=CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—$CH_2$C≡CH), pent-2-ynyl (—$CH_2$C≡$CCH_2$—$CH_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene (—C≡C—), propynylene (—$CH_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR*C(O)R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR*-alkyl, —OC(O)NR*-aryl, —OC(O)NR*-heteroaryl, and —OC(O)NR*-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR*C(O)O-alkyl, —NR*C(O)O-aryl, —NR*C(O)O-heteroaryl, and NR*C(O)O-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR*)—OR* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

"Halo" or "halogen" refers to fluoro, chloro, bromo and iodo.

"Heteroaryl" refers to a monovalent aromatic heterocyclic group which fulfils the Hückel criteria for aromaticity (ie. contains $4n+2$ $\pi$ electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl).

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

It will be understood that where Q is an optionally substituted heteroaryl or optionally substituted heterocyclyl which has one or more ring heteroatoms, the heteroaryl or heterocyclyl group can be connected to the core molecule of the compounds of the present invention, as represented by formulae (I) (Ia) (Ib) and (II), through a C—C or C-heteroatom bond, in particular a C—N bond.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylarnino" refers to the groups —NR*—P(O)(R)(OR*) where R* represents H, alkyl, cycloalkyl, alkenyl, or aryl, R represents OR* or is hydroxy or amino and R*** is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR*—, alkyl-S(O)—NR*—, cycloalkyl-S(O)—NR*—, aryl-S(O)—NR*—, heteroaryl-S(O)—NR*—, and heterocyclyl-S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR*—, alkyl-S(O)$_2$—NR*—, cycloalkyl-S(O)$_2$—NR*—, aryl-S(O)$_2$—NR*—, heteroaryl-S(O)$_2$—NR*—, and heterocyclyl-S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR*—, alkylO—S(O)—NR*—, cycloalkylO—S(O)—NR*—, arylO—S(O)—NR*—, heteroarylO—S(O)—NR*—, and heterocyclylO—S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR*—, alkylO—S(O)$_2$—NR*—, cycloalkylO—S(O)$_2$—NR*—, arylO—S(O)$_2$—NR*—, heteroarylO—S(O)$_2$—NR*—, and heterocyclylO—S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R*R*N—C(S)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR*—, alkyl-C(S)—NR*—, cycloalkyl-C(S)—NR*—, aryl-C(S)—NR*—, heteroaryl-C(S)—NR*—, and heterocyclyl-C(S)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R*R*N—S(O)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R*R*N—S(O)$_2$—, where each R* is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxyl, acyl, alkyl (which may be further substituted by amino, aminoacyl, oxyacyl, hydroxy, aryl and nitro), alkoxy, alkenyl, alkenyloxy, alkynyl, alkynyloxy, amino, aminoacyl, thio, arylalkyl, arylalkoxy (which may be further substituted by halogen, hydroxy, alkyl, nitro, alkoxy, acyl and amino), aryl (which may be further substituted by halogen, hydroxy, alkyl, nitro, alkoxy, acyl and amino), aryloxy (which may be further substituted by halogen, hydroxy, alkyl, nitro, alkoxy, acyl and amino), carboxyl, acylamino, cyano, halogen, nitro, phosphono, sulfo, phosphorylamino, phosphinyl, heteroaryl, heteroaryloxy, heterocyclyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin).

In some embodiments $R^{1A}$-$R^{1D}$ includes the following groups:

alkyl group, preferably methyl and ethyl;

substituted alkyl group, preferably 1-hydroxyethyl, 1-thioethyl, methoxyiminomethyl, ethoxyiminomethyl, 1-hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

acyl group, preferably formyl acetyl, propionyl, benzoyl (optionally substituted with methyl, methoxy, halogen, nitro, trifluoromethyl or cyano);

alkoxy group, preferably methoxy and ethoxy;

oxyacyl group, preferably methoxycarbonyl, ethoxycarbonyl, propoxycarbonyl, butyloxycarbonyl, isobutyloxycarbonyl;

acyloxy group, preferably acetoxy and propioxy;

substituted arylalkyl group, preferably 1-hydroxybenzyl, and 1-thiobenzyl;

sulfinyl group, preferably methylsulfinyl, ethylsulfinyl, benzene sulfinyl (optionally substituted with methyl, methoxy, halogen, nitro, trifluoromethane or cyano), methoxysulfinyl, ethoxysulfinyl;

sulfonyl group, preferably methylsulfonyl, ethylsulfonyl, benzenesulfonyl (optionally substituted with methyl, methoxy, halogen, nitro, trifluoromethane or cyano);

oxyacylamino group, preferably methoxycarbonylamido, and ethoxycarbonyl amido;

oxythioacyl group, preferably methoxythiocarbonyl and ethoxythiocarbonyl;

thioacyloxy group, preferably thionoacetoxy and thionopropionoxy;

sulphinylamino group, preferably methylsulfinylamino, ethylsulfinylamino, and benzenesulfinylamino (optionally substituted with methyl, methoxy, halogen, nitro, trifluoromethane or cyano);

amino group, preferably N-methylamino, and N,N'-dimethylamino;

substituted amino groups, preferably residues of L-valine, D-valine, L-alanine, D-alanine, aspartic acid, and alanylserine;

sulphonylamino group, preferably methylsulfonylamino, ethylsulfonylamino and benzene sulfonylamino (optionally substituted with methyl, methoxy, halogen, nitro, trifluoromethane or cyano);

substituted thio group, preferably alkylthio;

oxysulfinylamino group, preferably methoxysulfinylamino and ethoxysulfinylamino;

oxysulfonylamino group, preferably methoxysulfonylamino and ethoxysulfonylamino;

optionally substituted alkenyl group, preferably, 1-propenyl, vinyl, nitrovinyl, cyano vinyl, or trifluorovinyl and styryl (optionally substituted with methyl, methoxy, halogen, nitro, trifluoromethane or cyano);

alkynyl group, preferably 1-propynyl, ethynyl or trimethylsilylethynyl.

In a preferred embodiment Y represents a group of formula (i) where L is a carbonyl group (C=O) or a group of formula (ii).

Furthermore, it is preferred that $R^{1D}$ and $R^{1B}$ independently represent hydroxy or an ether substituent.

Accordingly, preferred compounds of the present invention are represented by formula (Ia)

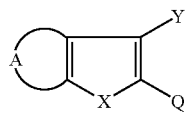
(Ia)

wherein;
X represents O, S, SO, SO$_2$, Se, SeO, or SeO$_2$;
A together with the atoms to which it is attached forms an optionally substituted heteroaryl or optionally substituted heterocyclyl;
═══ represents an optional double bond;
Y represents a group of formula (i)(a) or (ii);

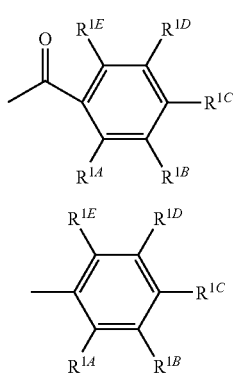

$R^{1A}$, $R^{1C}$ and $R^{1E}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy;
$R^{1D}$ and $R^{1B}$ independently represent hydroxy, optionally substituted arylalkoxy, optionally substituted alkenyloxy, optionally substituted alkoxy, optionally substituted alkynyloxy, or optionally substituted aryloxy; and
Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR", SR" or NR"R", where each R' independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl; and
wherein Y and Q do not represent the same group.

In an even more preferred embodiment, $R^{1A}$ and $R^{1E}$ represents H. In this embodiment it is preferred that $R^{1C}$ represents H, halogen, or an alkoxy group and $R^{1D}$ and $R^{1B}$ independently represent an alkoxy group. Most preferably $R^{1D}$, $R^{1C}$ and $R^{1B}$ represent an alkoxy group, and even more preferably a methoxy group.

Particularly preferred compounds of the present invention include those compounds where A is a bivalent linking group of 4 or 12 atoms selected from C, N, O and S. In that arrangement A and the atoms to which they are attached together form an optionally substituted heterocyclyl or heteroaryl ring having 6 to 14 ring atoms. Examples include where the substructure

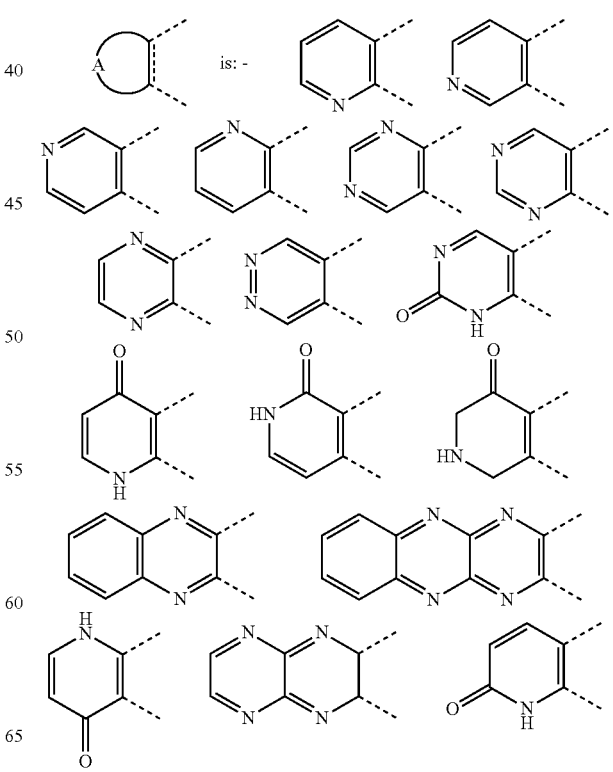

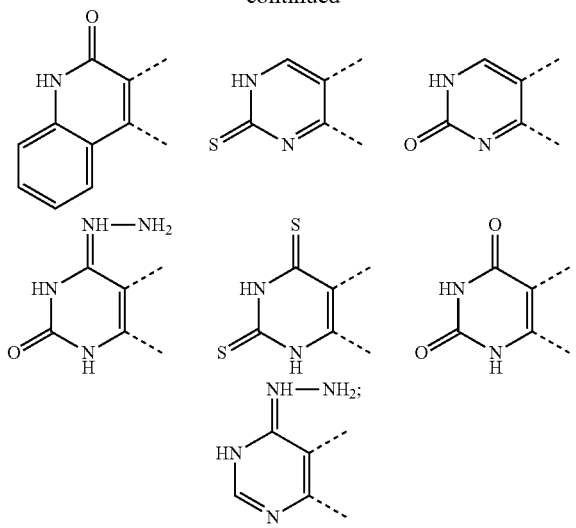

or substituted derivatives thereof.

More preferably A together with the atoms to which it is attached forms an optionally substituted 6-membered heteroaryl or optionally substituted 6-membered heterocycyl ring which contains at least one N-atom.

More preferably ring A is an optionally substituted phenyl, pyridyl, pyridinonyl, pyridazinyl, pyrimidinyl, pyrimidinonyl or pyrazinyl ring. Thus preferred compounds are those where ring A has the substructure:

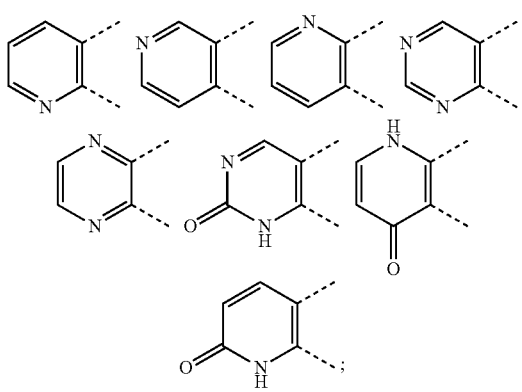

or substituted derivatives thereof.

The rings which represent A (and as depicted above) may be further optionally substituted, preferably by no more than 3 substituents. Of the optional substituents, it is particular preferred to use 1 to 3 substituents (and preferably 1 substituent) selected from halo, lower alkyl, halogenated forms of lower alkyl, hydroxy, lower alkoxy, nitro, amino, thio, optionally substituted lower alkylaryl, lower alkylamino, carboxy, and optionally substituted phenyl. N-oxide forms of the nitrogen atoms of nitrogen containing rings are also preferred. When A is a pyridyl ring, the ring nitrogen may be in a N-oxide form, or the ring may be in the form of a pyridinium salt.

Even more preferred compounds of the present invention are represented by formula (Ib)

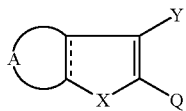

wherein;

X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

A together with the atoms to which it is attached forms an optionally substituted 6-membered heteroaryl or optionally substituted 6-membered heterocyclyl which contains at least one N-atom;

--- represents an optional double bond;

Y represents a group of formula (i)(b) or (ii)(a);

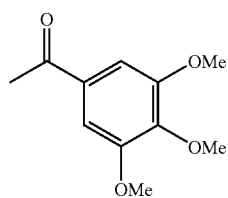

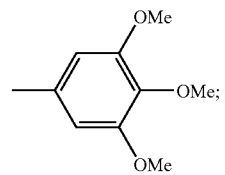

Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR'', SR'' or NR''R'', where each R' independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl; and wherein Y and Q do not represent the same group.

In this above embodiment (compounds of formula (Ib)) ring A is an optionally substituted phenyl, pyridyl, pyridinonyl, pyridazinyl, pyrimidinyl, pyrimidinonyl or pyrazinyl ring. Thus preferred compounds are those where ring A has the substructure:

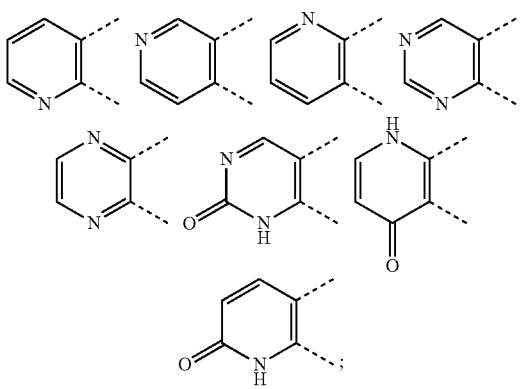

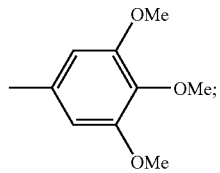

or substituted derivatives thereof.

Even more preferably (for compounds of formula (Ib)) ring A has the substructure:

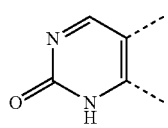

or substituted derivatives thereof.

Thus in an embodiment the compounds of the present invention are represented by formula (Ic)

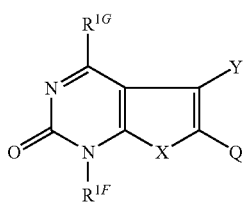

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1F}$ represents hydrogen, lower alkyl, lower alkylaryl, or optionally substituted phenyl;

$R^{1G}$ represents hydrogen, lower alkyl, lower alkoxy, lower alkylaryl, or optionally substituted phenyl;

Y represents a group of formula (i)(b) or (ii)(a);

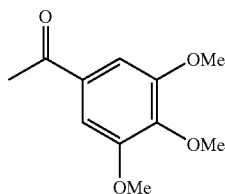

Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR″, SR″ or NR″′R″, where each R′ independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR″′NR″′, where each R″′ independently represents H, optionally substituted alkyl, optionally substituted alkenyl, optionally substituted alkynyl, optionally substituted aryl and optionally substituted heteroaryl; and wherein Y and Q do not represent the same group.

In the above embodiment preferably, $R^{1F}$ is hydrogen or lower alkyl and $R^{1G}$ is hydrogen.

For the compounds represented by formulae (I), (Ia), (Ib), (Ic) and (II), X is preferably selected from O and S. More preferably X is O.

Furthermore, for the compounds of formulae (I), (Ia), (Ib), (Ic) and (II) it is preferred that Q represents an optionally substituted aryl or optionally substituted heteroaryl group.

Accordingly, preferred compounds are represented by formulae (I), (Ia), and (Ib) where X is O, Y represents a group of formula (i)(b) or (ii)(a), A together with the atoms to which it is attached forms an optionally substituted 6-membered heteroaryl or optionally substituted 6-membered heterocyclyl which contains at least one N-atom, and Q represents an optionally substituted aryl group or an optionally substituted heteroaryl group (and wherein Y and Q are not the same group).

In the above mentioned embodiments (i.e., compounds of formulae (I), (Ia), (Ib), (Ic), and (II)), Q more preferably represents an optionally substituted phenyl group or a 5 or 6 membered optionally substituted heteroaryl group, preferably having from 1 to 4 heteroatoms selected from O, S, Se, or N and mixtures thereof.

Examples of preferred 5 membered optionally substituted heteroaryl groups include optionally substituted imidazolyl, optionally substituted triazolyl, optionally substituted pyrrolyl, optionally substituted pyrazolyl, optionally substituted thiazolyl, optionally substituted thiophenyl, optionally substituted furanyl, optionally substituted selenophenyl, optionally substituted oxazolyl, optionally substituted isoazolyl, optionally substituted isothiazolyl, optionally substituted oxadiazolyl, optionally substituted thiadiazolyl, optionally substituted tetrazolyl, optionally substituted oxatriazolyl, optionally substituted thiatriazolyl, optionally substituted indolyl, optionally substituted benzofuranyl and optionally substituted benzothiophenyl.

Examples of preferred 6 membered optionally substituted heteroaryl groups include optionally substituted pyridinyl, optionally substituted pyrimidinyl, optionally substituted pyronyl, optionally substituted coumarinyl, optionally substituted chromonyl, optionally substituted pyridonyl, optionally substituted purinyl (adeninyl and guaninyl), optionally substituted uracilyl, optionally substituted thymidinyl, optionally substituted cytosinyl, optionally substituted quinolinyl and optionally substituted isoquinolinyl.

Examples of more preferred 5 to 6 membered heteroaryl groups include: indolyl, 1-methyl-indolyl, furanyl, pyrazolyl and pyridinyl.

The compounds of the present invention can be prepared based on modification of the multicomponent reaction system which has been described in PCT/AU02/00099 (WO 02/060872), the entire contents of which is incorporated herein by reference. In particular the compounds of the present invention can be prepared by the reaction sequences depicted in Scheme 1 below:

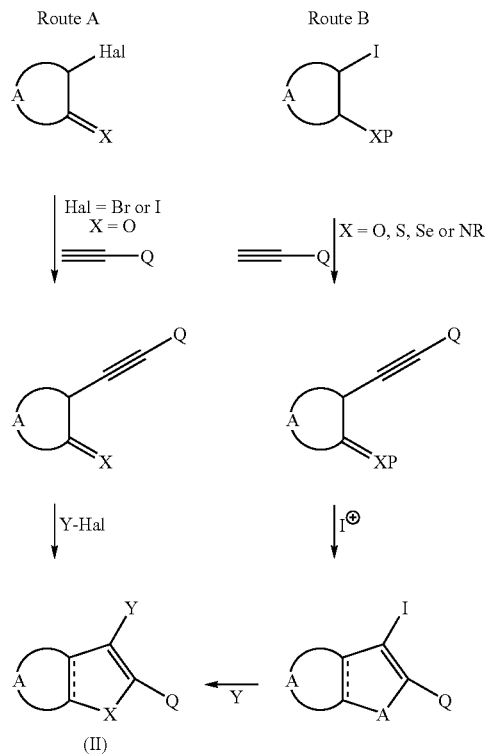

Scheme 1

As shown in scheme 1 (referring to Route A) the compounds of formula (II) in which X=O can be derived from reacting together a heteroaryl or heterocyclic group, which bears a suitably positioned carbonyl group adjacent to a sufficiently reactive halogen (preferably I), with a terminal alkyne. These starting compounds can be coupled together under conditions known in the art, for example, using nickel or palladium based coupling agents such as Pd $(PPh_3)_2Cl_2$ or Pd $(PPh_3)_4$. Preferably a copper co-catalyst such as CuI is added together with a suitable base such as a trialkylamine (ie under Sonogashira conditions). With the coupling of the alkyne, cyclisation can be afforded by reaction with a group Y-Hal (preferably Y—I) again under palladium catalysed coupling conditions. In this embodiment Y and Q are preferably optionally substituted phenyl groups. It is also possible to produce compounds where Q is an optionally substituted phenyl group and Y is an optionally substituted aroyl group. This involves the reaction of the alkyne intermediate with a compound of formula Y-Hal under carbonylative Pd based coupling conditions (ie under CO).

Route B depicts an alternative protocol to access compounds of formula (II) where X is O, S, Se, or NR. P is a suitable protective group. For instance, when X is Se, O or S, P may be a methyl group. Where X is NR, the nitrogen atom of the starting aniline is suitably protected by a nitrogen protecting group or as an imine. Suitable nitrogen protecting groups are known to those skilled in the art of organic synthesis and include acyl groups (eg acetyl, trifluoroacetyl), phenyl, benzyl and benzoyl. Other suitable nitrogen protecting groups may be found in *Protective Groups in Organic Synthesis*, T. W. Greene and P. Wutz, John Wiley & Son, 3$^{rd}$ Edition.

As shown above in Route B, the compounds of formula (II) in which X is NR, O, Se or S can be prepared by reacting together a protected phenol, protected thiol, protected selenol, or protected amine and terminal alkyne respectively.

The protected X group (which bears a suitably positioned adjacent halogen, preferably I) may be coupled together using, for instance, the Sonogashira methodology described above in Route A. Alternatively, the coupling may be carried out under Negishi conditions with the use of an alkyllithium, $ZnBr_2$ and a Pd catalyst. The coupling reaction may be performed under conditions which allow for heteroannulation to spontaneously occur so as to form the target hetero-fused furan, thiophene, etc in a "one-pot" synthetic strategy. This may involve the addition of iodine or another $I^\oplus$ source after the initial coupling reaction to effect iodocyclisation.

The Y group may be introduced again by suitable Pd based coupling chemistry. For instance, an aryl or aroyl group may be exchanged for the I atom or Sn group under Stille cross-coupling reactions using stannanes (eg, aryl or alkylstannanes), Suzuki conditions (with boronic acids/esters) or by carbonylative Suzuki or Stille conditions.

The Pd catalysed coupling reactions discussed above are generally performed at temperatures below room temperature, most preferably at 0° C. and below (for instance at −78° C.). It is also preferred that such reactions are carried out under an inert atmosphere of either nitrogen or argon. Suitable solvents include solvents such as THF, diethyl ether, DMSO, dioxane, acetonitrile, dichloromethane, etc.

As stated earlier the intermediates can be reacted, in situ, with Halogen-Y in the presence of a palladium catalyst in an atmosphere of CO to compounds of formula (II) where Y is aroyl. This may be accomplished by evacuating the inert reaction gas present in the initial coupling step and replacing said gases with CO. In this system it is also preferred that the initial reaction solvent is replaced with a more polar solvent such as, for instance, DMSO. Removal of the initial reaction solvent may be achieved in vacuo.

SO, $SO_2$, SeO, and $SeO_2$ derivatives can be prepared by controlled oxidation of the corresponding sulphides (ie, where L=S) and selenides (ie where L=Se), respectively.

Other compounds of formula (II) can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

Examples of functional group inter-conversions are: —C(O)NR*R** from —$CO_2CH_3$ by heating with or without catalytic metal cyanide, e.g. NaCN, and HNR*R** in CH$_3$OH; —OC(O)R from —OH with e.g., ClC(O)R in pyridine; —NC(S)NR*R** from —NHR with an alkylisothiocyanate or thiocyanic acid; —NRC(O)OR* from —NHR with alkyl chloroformate; —NRC(O)NR*R** from —NHR by treatment with an isocyanate, e.g. HN=C=O or RN=C=O; —NRC(O)R* from —NHR by treatment with ClC(O)R* in pyridine; —C(=NR)NR*R** from —C(NR*R**)SR with H$_3$NR=OAc$^-$ by heating in alcohol; —C(NR*R**)SR from —C(S)NR*R** with R—I in an inert solvent, e.g. acetone; —C(S)NR*R** (where R* or R** is not hydrogen) from —C(S)NH$_2$ with HNR*R**; —C(=NCN)—NR*R** from —C(=NR*R**)—SR with NH$_2$CN by heating in anhydrous alcohol, alternatively from —C(=NH)—NR*R** by treatment with BrCN and NaOEt in EtOH; —NR—C(=NCN)SR from —NHR* by treatment with (RS)$_2$C=NCN; —NR**SO$_2$R from —NHR* by treatment with ClSO$_2$R by heating in pyridine; —NR*C(S)R from —NR*C(O)R by treatment with Lawesson's reagent [2,4-bis(4-methoxyphenyl)-1,3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR* with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R* from R$^C$(O)R* by R**CO$_3$H; —CCH$_2$OH from —C(O)OR* with Na/R**OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from CN with SnCl$_2$/HCl; —CN from —C(O)NHR with PCl$_5$; —CH$_2$R from —C(O)R with N$_2$H$_4$/KOH.

An important aspect of the present invention relates to compounds which possess tubulin binding activity. In particular it has been found that the introduction of the hetero A ring system, can give rise to improved pharmacological properties over the same compounds which are based on a benzofused framework (ie benzothiophenes, benzofurans, benzoselenophenes and indoles). In particular it is envisaged that such compounds possess better solubility and therefore possess improved pharmacokinetic properties over the benzofused analogues.

As mentioned previously, preferred compounds of the invention having improved tubulin binding activity or antitumour vasculature activity, can be useful in methods of therapy. In particular these compounds may be used for treating tumours. As used herein the term "tumour" is used to define any malignant cancerous growth, and may include leukemias, melanomas, colon, lung, ovarian, skin, breast, prostate, CNS, and renal cancers, as well as other cancers.

The compounds of the invention having tubulin binding activity may also be used in the treatment of solid tumours, eg. breast cancer.

The invention also provides for the use of a compound of formula (I), (Ia), (Ib), (Ic), or (II) in the manufacture of a medicament for treating tumours.

There is also provided a method of treatment of solid tumours comprising the administration of an effective amount of a compound of formula (I), (Ia), (Ib), (Ic), or (II) to a subject in need thereof.

The compounds of the invention may be particularly useful in combination therapy, eg. combining the treatment with other chemotherapeutic or radiation treatments.

However, it will be understood that the compounds of the invention can be used in the treatment of any disease state for which tubulin polymerisation plays a crucial role.

In particular, the present compounds can be used in treating inflammation. Such inflammatory conditions may include acute and chronic inflammatory conditions such as rheumatoid arthritis, inflammatory bowel disease, Crohn's disease, psoriasis, and the like.

Compounds of the invention which possess bioactivity, such as tubulin binding activity, can be formulated as a composition, particularly a pharmaceutical composition, together with a pharmaceutically acceptable additive.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients.

In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Preferably, the compounds of the present invention may be administered to a subject as a pharmaceutically acceptable salt. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a compound of formula (I), (Ia), (IIb), or (II) is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate or phosphate ester, or where a free amino group is converted into an amide (eg. α-aminoacid amide). Procedures for esterifying, eg. acylating, the compounds of the invention are well known in the art and may include treatment of the compound with an appropriate carboxylic acid, anhydride or chloride in the presence of a suitable catalyst or base. A particularly preferred prodrug is a disodium phosphate ester. The disodium phosphate ester of novel compounds of the invention may be useful in targeting tumour vasculature and thus may provide a means of selective delivery of the compounds to the body. The disodium phosphate ester may be prepared in accordance with the methodology described in Pettit, G. R., et al, *Anticancer Drug Des.,* 1995, 10, 299.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, eg., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

The synthetic methods and processes described herein to prepare the compounds of the present invention are amenable to solid phase synthetic techniques and/or combinatorial chemistry to produce individual compounds or libraries of compounds.

Traditionally, drug candidates have been synthesised individually, this being a time consuming and laborious process if the synthetic sequence contains even just a few steps and large numbers of compounds are to be evaluated for their biological activity. Combinatorial synthesis is an emerging technique for effecting the generation of large libraries of molecules and has been successfully exploited in the synthesis and evaluation of small organic libraries. These libraries and their starting substrates may exist as molecules in free solution or preferably, linked to a solid support, for example, beads, pins, microtitre plates (wells) or microchips which can be polymeric, glass, silica or other suitable substrate. Chemical diversity can be achieved by either parallel or split (split and mix) syntheses wherein each step has the potential to afford a multitude of compounds. Solution phase libraries may be prepared via parallel syntheses wherein different compounds are synthesised in separate reaction vessels in parallel, often in an automated fashion. Alternatively, attachment of the individual components employed in a synthetic sequence to an appropriate solid phase support allows for the further creation of chemical diversity by utilising not only parallel synthesis but also split synthesis wherein the solid support containing the compounds prepared in the prior step can be split into a number of batches, treated with the appropriate reagent and recombined.

The substrates can be attached to a solid support surface by any linkers known in the art. The linkers may be any component capable of being cleaved to release the substrate or final compound from the support.

Preferably, the solid support is a polymer support. Examples of polymeric supports currently used in solid phase synthesis include: alkenyl resins: eg. REM resins; BHA resins: eg. benzhydrylamine (polymer-bound hydrochloride, 2% crosslinked), benzhydryl chloride (polymer bound); Br-functionalised resins: eg. brominated PPOA resin, brominated Wang resin; Chloromethyl resins: eg. 4-methoxybenzhydryl chloride (polymer bound); CHO-functionalised resins: eg. indole resin, formylpolystyrene; Cl-functionalised resins: eg. Merrifield's resin, chloroacetyl (polymer bound); $CO_2H$-functionalised resins: eg. carboxypolystyrene; I-functionalised resins: eg. 4-iodophenol (polymer bound); Janda Jels™; MBHA resins: eg. 4-methylbenzhydrylamine hydrochloride (polymer bound), 4-hydroxymethylbenzoic acid-4-methyl benzhydrylamine (polymer bound); Amine-functionalised resins: eg. (aminomethyl)polystyrene, PAL resin, Sieber amide resin; Nitrophenyl carbonate resins: eg. 4-nitrophenyl carbonate (polymer bound); OH-functionalised resins: eg. 4-benzyloxybenzyl alcohol (polymer bound); Hydroxy methyl resins: eg. benzyl alcohol (polymer bound); HMBA resin; Oxime resins; Rink acid resin; Triazine-based resin; Trityl amine resins; Trityl resins: eg. trityl-chloride (polymer bound), 2-chlorotrityl alcohol, 1,3-diaminepropane trityl.

Thus, individual compounds or libraries of compounds can be synthesised by initially attaching the first compound substrate to a solid support surface which can be performed by providing a plurality of solid support surfaces, suitably derivatising each of the surfaces with groups capable of reacting with either the compound substrate or a linker moiety attached thereto. The various support surfaces with the attached first compound substrate can then be subjected to various reaction conditions and second compound substrates to provide a library of attached compounds, which may, if necessary, be reacted further with third and subsequent compound substrates or varying reactions conditions. Attachment and detachment of substrates and products can be performed under conditions similar to those as described in Johnson, M. G., et al., *Tetrahedron,* 1999, 55, 11641; Han Y., et al. *Tetrahedron* 1999, 55, 11669; and Collini, M. D., et al., *Tetrahedron Lett.,* 1997, 58, 7963.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Biological Data

TABLE 1

In vitro Data for Compounds: Inhibition of tubulin polymerisation and/or Inhibition of Proliferation of activated HUVEC cells.

| Entry (Example) | Structure | TPI, IC$_{50}$ (μM)[1] | Activated HUVECs IC$_{50}$ (nM)[2] |
|---|---|---|---|
| 1. | 5-(3,4,5-trimethoxyphenyl)-6-(4-methoxyphenyl)furo[2,3-d]pyrimidin-2(1H)-one | 2.0 | 10–100 |
| 2. | 5-(4-methoxyphenyl)-6-(3,4,5-trimethoxyphenyl)furo[2,3-d]pyrimidin-2(1H)-one | 4–10 | 100–1000 |
| 3. | 5-(3,4,5-trimethoxyphenyl)-6-(furan-2-yl)furo[2,3-d]pyrimidin-2(1H)-one | | >1000 |
| 4. | 5-(3,4,5-trimethoxyphenyl)-6-(1-methyl-1H-indol-5-yl)furo[2,3-d]pyrimidin-2(1H)-one | | 1–10 |

TABLE 1-continued

In vitro Data for Compounds: Inhibition of tubulin polymerisation and/or Inhibition of Proliferation of activated HUVEC cells.

| Entry (Example) | Structure | TPI, IC$_{50}$ (μM)[1] | Activated HUVECs IC$_{50}$ (nM)[2] |
|---|---|---|---|
| 5. | 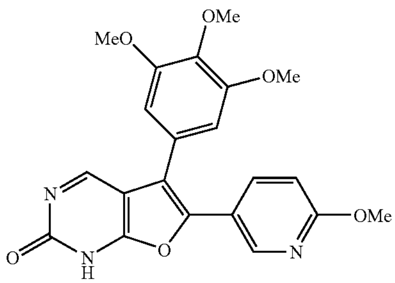 [SMILES: COc1ccc(-c2oc3[nH]c(=O)ncc3c2-c2cc(OC)c(OC)c(OC)c2)cn1] | | 100-1000 |
| 6. | 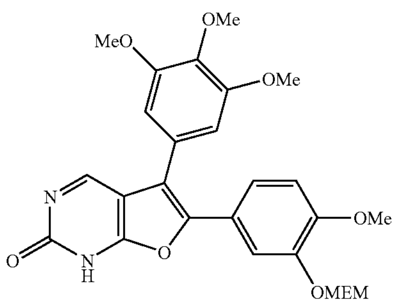 | | |
| 7. | 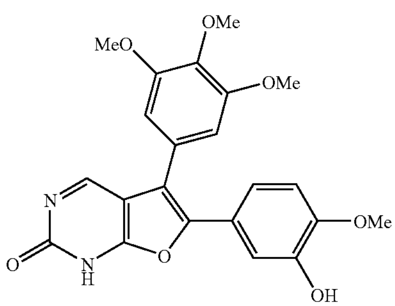 [SMILES: COc1ccc(-c2oc3[nH]c(=O)ncc3c2-c2cc(OC)c(OC)c(OC)c2)cc1O] | | 10-100 |
| 8. | 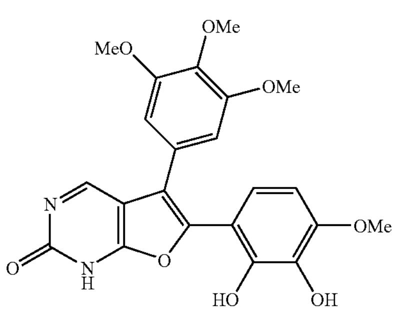 [SMILES: COc1ccc(-c2oc3[nH]c(=O)ncc3c2-c2cc(OC)c(OC)c(OC)c2)c(O)c1O] | | >1000 |

TABLE 1-continued

In vitro Data for Compounds: Inhibition of tubulin polymerisation and/or Inhibition of Proliferation of activated HUVEC cells.

| Entry (Example) | Structure | TPI, IC$_{50}$ (μM)[1] | Activated HUVECs IC$_{50}$ (nM)[2] |
|---|---|---|---|
| 9. | 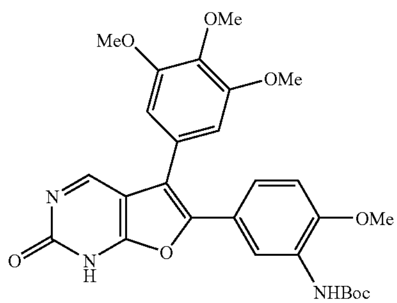 | ND | ND |
| 10. | 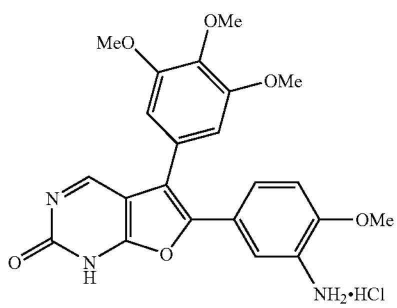 | | >1000 |
| 11. | 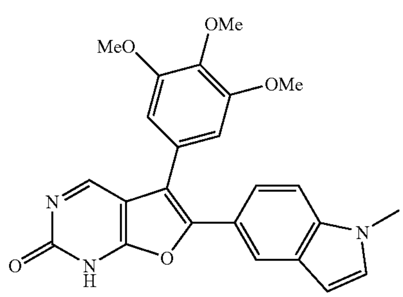 [SMILES: COc1cc(-c2c(-c3ccc4c(ccn4C)c3)oc3[nH]c(=O)ncc23)cc(OC)c1OC] | ND | ND |
| 12. | 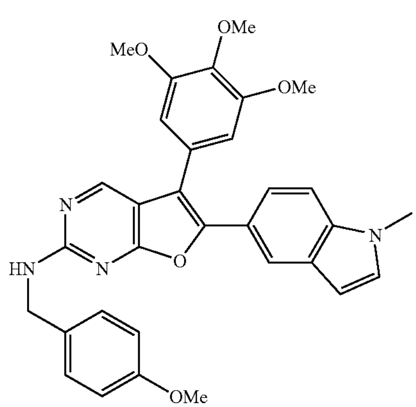 [SMILES: COc1ccc(CNc2ncc3c(-c4cc(OC)c(OC)c(OC)c4)c(-c4ccc5c(ccn5C)c4)oc3n2)cc1] | ND | ND |

TABLE 1-continued

In vitro Data for Compounds: Inhibition of tubulin polymerisation and/or Inhibition of Proliferation of activated HUVEC cells.

| Entry (Example) | Structure | TPI, IC$_{50}$ (μM)[1] | Activated HUVECs IC$_{50}$ (nM)[2] |
|---|---|---|---|
| 13. | 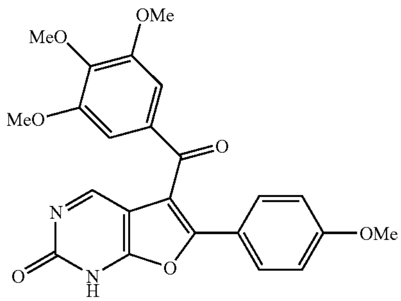 [SMILES: COc1ccc(-c2oc3[nH]c(=O)ncc3c2C(=O)c2cc(OC)c(OC)c(OC)c2)cc1] | >40 | ND |
| 14. | 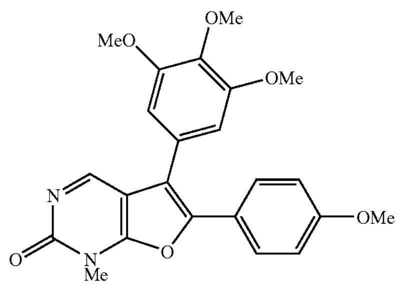 [SMILES: COc1ccc(-c2oc3c(cnc(=O)n3C)c2-c2cc(OC)c(OC)c(OC)c2)cc1] | ND | ND |
| 15. | 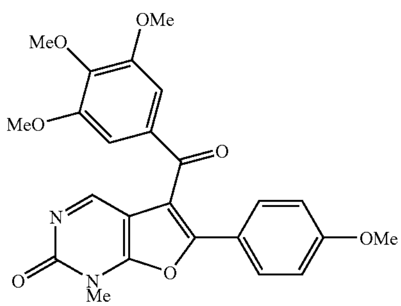 [SMILES: COc1ccc(-c2oc3c(cnc(=O)n3C)c2C(=O)c2cc(OC)c(OC)c(OC)c2)cc1] | >40 | ND |
| 16. | 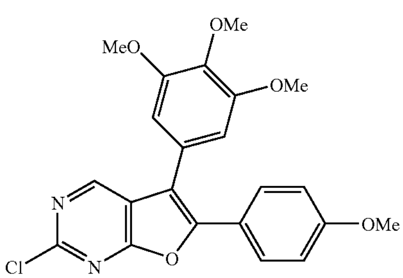 [SMILES: COc1ccc(-c2oc3nc(Cl)ncc3c2-c2cc(OC)c(OC)c(OC)c2)cc1] | 10-40 | ND |
| 17. | 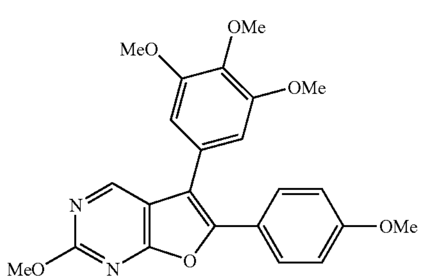 | >40 | ND |

TABLE 1-continued

In vitro Data for Compounds: Inhibition of tubulin polymerisation and/or Inhibition of Proliferation of activated HUVEC cells.

| Entry (Example) | Structure | TPI, IC$_{50}$ (µM)[1] | Activated HUVECs IC$_{50}$ (nM)[2] |
|---|---|---|---|
| 18. | 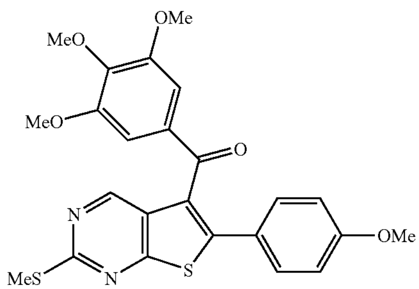 [SMILES: COc1ccc(-c2sc3nc(SC)ncc3c2C(=O)c2cc(OC)c(OC)c(OC)c2)cc1] | >40 | ND |
| 19. | 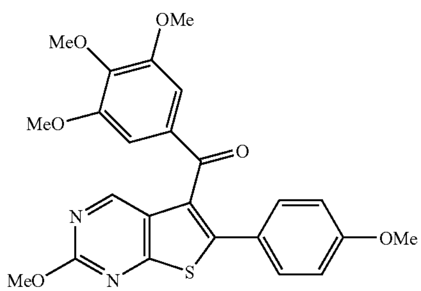 | >40 | >1000 |
| 20. | 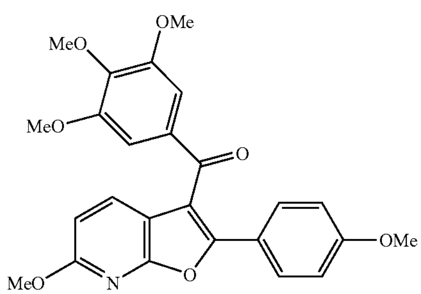 [SMILES: COc1ccc(-c2oc3nc(OC)ccc3c2C(=O)c2cc(OC)c(OC)c(OC)c2)cc1] | ~2 | 100-1000 |
| 21. | 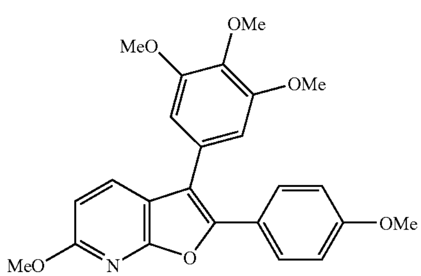 | >40 | ND |
| 22. | 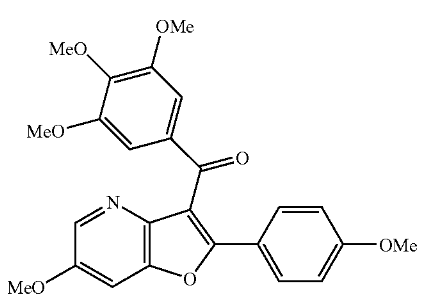 [SMILES: COc1ccc(-c2oc3cc(OC)cnc3c2C(=O)c2cc(OC)c(OC)c(OC)c2)cc1] | <4 | 100-1000 |

TABLE 1-continued

In vitro Data for Compounds: Inhibition of tubulin polymerisation and/or Inhibition of Proliferation of activated HUVEC cells.

| Entry (Example) | Structure | TPI, IC$_{50}$ (μM)[1] | Activated HUVECs IC$_{50}$ (nM)[2] |
|---|---|---|---|
| 23. | 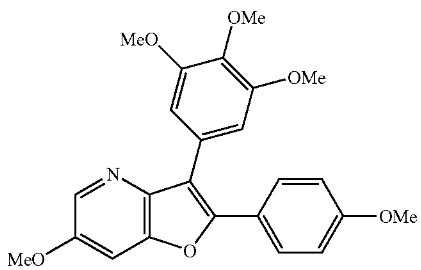 [SMILES: COc1ccc(-c2oc3cc(OC)cnc3c2-c2cc(OC)c(OC)c(OC)c2)cc1] | ~10 | >1000 |
| 24. | 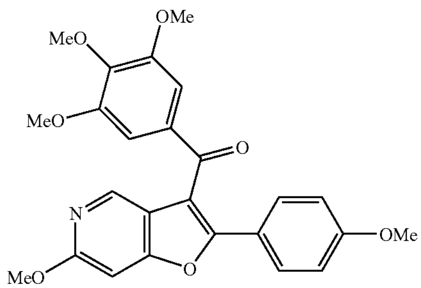 | <4 | 100-1000 |
| 25. | 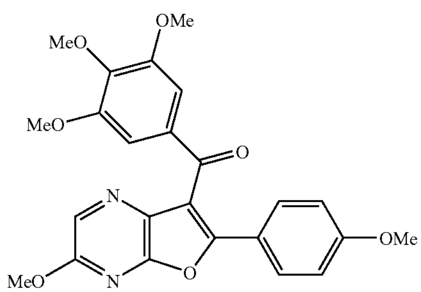 [SMILES: COc1ccc(-c2oc3nc(OC)cnc3c2C(=O)c2cc(OC)c(OC)c(OC)c2)cc1] | <4 | 10-100 |
| 26. | 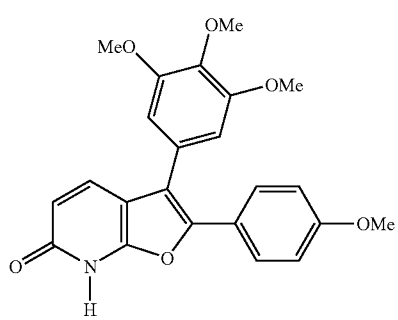 [SMILES: COc1ccc(-c2oc3[nH]c(=O)ccc3c2-c2cc(OC)c(OC)c(OC)c2)cc1] | | 100-1000 |
| 27. | 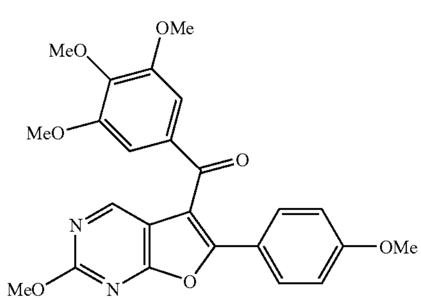 [SMILES: COc1ccc(-c2oc3nc(OC)ncc3c2C(=O)c2cc(OC)c(OC)c(OC)c2)cc1] | | 100-1000 |

TABLE 1-continued

In vitro Data for Compounds: Inhibition of tubulin polymerisation and/or Inhibition of Proliferation of activated HUVEC cells.

| Entry (Example) | Structure | TPI, IC$_{50}$ (μM)[1] | Activated HUVECs IC$_{50}$ (nM)[2] |
|---|---|---|---|
| 28. | (structure shown) | | 100-1000 |
| 29. | (structure shown) | | |
| 30. | (structure shown) | | >1000 |

[1]Tubulin polymerisation inhibitor (TPI) assay. IC$_{50}$ is the concentration required to inhibit the extent of tubulin polymerisation by 50%. For method see: Flynn, B. L.;Verdier-Pinard, P.; Hamel, E. Org. Lett. 2001, 3, 651 and refs cited there-in.

[2]Activated human umbilical vein endothelial cells (HUVECs). IC$_{50}$ is the concentration required to inhibit proliferation by 50%, this value falls within the range of concentrations given or >1000 nM

Synthetic Protocols

General Procedure 1:

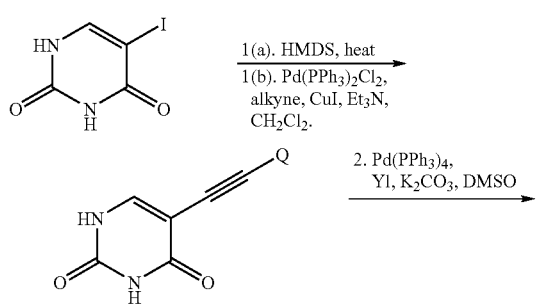

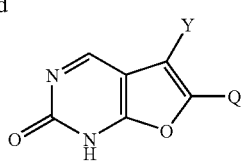

Step 1: 5-Iodouracil (1 mmol) was refluxed in hexamethyldisilazide (HMDS) (2 ml) and trimethylsilylchloride TMSCl (3 drops) in round bottom flask under a nitrogen atmosphere and until all solids had dissolved (ca 2 h). The excess of HMDS was removed under vacuum and the oily residue was dried under high vacuum. The dried oil was dissolved in mixture of anhydrous dichloromethane (4 ml) and NEt$_3$ (2 ml) and the system was evacuated-back filled with N$_2$ three times before adding Pd(PPh$_3$)$_2$Cl$_2$ (or Pd(PPh$_3$)

4) (3 mol %), alkyne (1.3 mmol) and CuI (16 mg, 8 mol %). The system was again quickly evacuated and back filled with N$_2$ and then stirred at room temp for overnight. The reaction was quenched by addition of 2 ml of MeOH with stirring for 15 min. The solvents removed under vacuum and the brownish residue was purified as described for each example (below).

Step 2: The 5-alkynyluracil (1.0 mmol), anhydrous K$_2$CO$_3$ (0.41 g, 3.0 mmol), aryliodide (1.1 mmol) and Pd(PPh$_3$)$_2$Cl$_2$ (or Pd(PPh$_3$)$_4$) (5 mol %) were added to dry round bottom flask under N$_2$ atmosphere. The system was evacuated and back filled with N$_2$ and then anhydrous DMSO (10 ml) was added. The system was again evacuated and back-filled with N$_2$ three times and heated to 100-110° C. with stirring overnight. The solvents were removed under vacuum and residue dissolved in EtOAc (50 ml) and washed with water (20 ml). The aqueous layer was further extracted with EtOAc (3×30 ml). The organic layers were collected, dried and evaporated. The residue was purified as described for each example (below).

Example 1

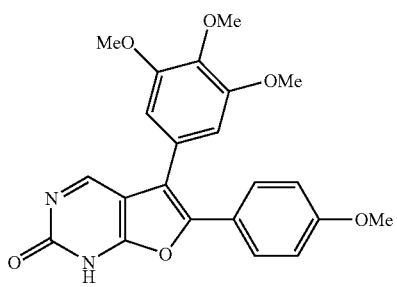 [SMILES: COc1ccc(-c2oc3[nH]c(=O)ncc3c2-c2cc(OC)c(OC)c(OC)c2)cc1]

6-2-(4-methoxyphenyl))5(3,4,5-trimethoxyphenyl) furo[2,3-d]pyrimidin-2(1H)-one

Prepared according to General Procedure 1

Step 1: 5-iodouracil (0.5 g, 2.10 mmol) and 1-ethynyl-4-methoxybenzene (0.81 g, 4.20 mmol). The crude reaction mixture was diluted with ethyl acetate (300 mL) and washed with H$_2$O (2×300 mL, 50 mL brine added). The aqueous extracts were combined, and sat. NH$_4$Cl solution (100 mL) added. The aqueous phase was then washed with ethyl acetate (2×350 mL), the organics combined, dried (MgSO$_4$), filtered and concentrated to give the coupled alkyne as a white cream solid (0.42 g, 83%) give the coupled product as a white cream solid (0.42 g, 83%). $^1$H NMR (300 MHz, DMSO-d$_6$): δ 11.33 (br s, 2H), 7.80 (s, 1H), 7.38 (d, J=8.7 Hz, 2H), 6.94 (d, J=8.7 Hz, 2H), 3.77 (s, 3H).

Step 2: The product from step 1 (0.24 g, 1.0 mmol), 3,4,5-trimethoxyiodobenzene (0.32 g, 1.1 mmol) and Pd(PPh$_3$)$_4$ (57 mg, 0.05 mmol) were added followed by DMSO (10 mL). The stirred mixture was heated to 100° C. overnight, diluted with ethyl acetate (300 mL) and washed with sat. NH$_4$Cl solution (5%, 200 mL). The aqueous phase was washed with ethyl acetate (3×200 mL), the organic extracts combined, dried (MgSO$_4$), filtered and concentrated to give the desired cyclised product as a pale brown solid which was chromatographed on silica gel (CH$_2$Cl$_2$, EtOAc and methanol 10:10:1) to give the pure product (0.34 g, 83%). $^1$H NMR (300 MHz, CDCl$_3$): δ 7.99 (s, 1H), 7.61 (d, J=9.0 Hz, 2H), 6.87 (d, J=9.0 Hz, 2H), 6.62 (s, 2H), 3.94 (s, 3H), 3.83 (s, 3H), 3.81 (s, 6H). MS (ESI, 409 [M+H]$^+$).

Example 2

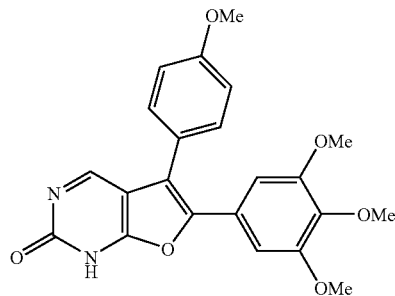 [SMILES: COc1ccc(-c2c(-c3cc(OC)c(OC)c(OC)c3)oc3[nH]c(=O)ncc23)cc1]

6-(2-(3,4,5-trimethoxyphenyl))-5-(4-methoxyphenyl) furo[2,3-d]pyrimidin-2(1H)-one Prepared according to General Procedure 1

Step 1: 5-iodouracil (2.10 mmol) and 1-ethynyl-3,4,5-trimethoxybenzene (4.20 mmol). The crude reaction mixture was diluted with ethyl acetate (300 mL) and washed with H$_2$O (2×300 mL, 50 mL brine added). The aqueous extracts were combined, and sat. NH$_4$Cl solution (100 mL) added. The aqueous phase was then washed with ethyl acetate (2×350 mL), the organics combined, dried (MgSO$_4$), filtered and concentrated to give the coupled alkyne as a white cream solid (0.49 g, 78%). $^1$H NMR (300 MHz, DMSO-d$_6$): δ 11.37 (br s, 1H), 11.24 (br s, 1H), 7.83 (s, 1H), 6.71 (s, 1H), 3.76 (s, 6H), 3.65 (s, 3H).

Step 2: The product from step 1 (0.32 mmol), 4-methoxy-iodobenzene (0.35 mmol) The aqueous phase was washed with ethyl acetate (3×200 mL), the organic extracts combined, dried (MgSO$_4$), filtered and concentrated to give the desired cyclised product as a pale brown solid which was chromatographed on silica gel (CH$_2$Cl$_2$, EtOAc and methanol 10:10:1) to give the pure product (93 mg, 69%). $^1$H NMR (300 MHz, DMSO-d$_6$): δ 8.08 (s, 1H), 7.42 (d, J=8.4 Hz, 2H), 7.04 (d, J=8.4 Hz, 2H), 6.75 (s, 2H), 3.77 (s, 3H), 3.65 (s, 3H), 3.59 (s, 6H).

Example 3

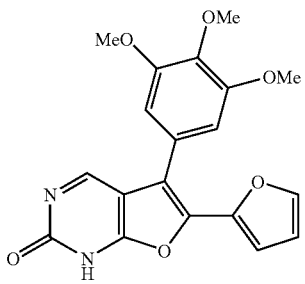 [SMILES: COc1cc(-c2c(-c3ccco3)oc3[nH]c(=O)ncc23)cc(OC)c1OC]

6-(2-furyl)-5-(3,4,5-trimethoxyphenyl)furo[2,3-d]pyrimidin-2(1H)-one

Prepared According to General Procedure I

Step 1: 5-iodouracil was coupled to 2-ethynylfuran. After quenching the reaction with MeOH the yellow powder was washed with MeOH and then with $CH_2Cl_2$. The yellow powder was dried under vacuum and used as such without further purification Yield (65%). $^1$H NMR (300 MHz, DMSO-d6) δ: 6.67 (dd, J1=3.6, J2=1.5, 1H), 6.92 (d, 3.6, 1H), 7.86 (d, J=1.5, 1H), 7.98 (s, 1H), 11.28 (bs, 1H, NH), 11.38 (bs, 1H, NH).

Step 2: The coupled product from Step 1 was coupled with 3,4,5-trimethoxyiodobenzene. EtOAc extract was evaporated and purified by silica gel column chromatography using increasing gradient of EtOAc in $CH_2Cl_2$ (23%). $^1$H NMR (300 MHz, DMSO-d6) δ: 3.69 (s, 3H, OMe), 3.76 (s, 6H, 2×OMe), 6.63 (dd, J=3.6, J=1.5 Hz, 1H), 6.82 (s, 2H), 6.85 (d, 3.6, 1H), 7.82 (d, J=1.5, 1H), 8.29 (s, 1H).

Example 4

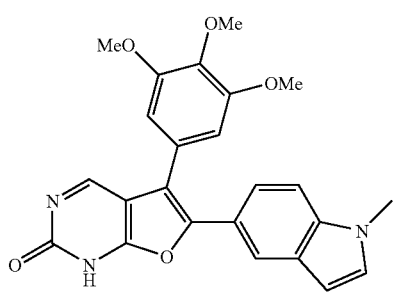 [SMILES: COc1cc(-c2c(-c3ccc4c(ccn4C)c3)oc3[nH]c(=O)ncc23)cc(OC)c1OC]

6-(1-Methyl-1H-indol-5-yl)-5-(3,4,5-trimethoxyphenyl)-1H-furo[2,3-d]pyrimidin-2-one Prepared According to General Procedure 1:

Step 1: 5-iodouracil was coupled to 5-ethynyl-1-methyl-1H-indole (see below). After quenching reaction mixture with MeOH, the yellowish solid was suspended in $CH_2Cl_2$ sonicated, filtered and washed with $CH_2Cl_2$ thoroughly. Similarly washed with MeOH and dried under high vacuum; Yield (80%); $^1$H NMR (300 MHz, DMSO-d6) δ: 3.76 (s, 3H, OMe), 6.41 (d, J=3.0, 1H), 7.18 (dd, J=8.7, J2=1.2, 1H), 7.34 (d, J=3.0, 1H), 7.42 (d, J=8.7, 1H), 7.64 (s, 1H), 7.79 (s, 1H), 11.15 (bs, 1H, NH), 11.34 (bs, 1H, NH).

Step 2: The material from step 1 was coupled to 3,4,5-trimethoxyiodobenzene. After evaporation of DMSO, the reaction mixture was diluted with EtOAc and washed with small amount of water. The residue was purified by column chromatography using 5% MeOH in 1:1 mixture of EtOAc and $CH_2Cl_2$. $^1$H NMR (300 MHz, DMSO-d6) δ: 3.65 (s, 6H, 2×OMe), 3.70 (s, 3H, OMe), 3.76 (s, 3H, OMe), 6.45 (d, J=3.0 Hz, 1H), 6.73 (s, 2H), 7.28 (dd, J=8.7, 1.2 Hz, 1H), 7.34 (d, J=3.0 Hz, 1H), 7.43 (d, J=8.7 Hz, 1H), 7.83 (d, J=1.3 Hz, 1H), 8.18 (s, 1H).

5-ethynyl-1-methyl-1H-indole: This material was prepared by N-methylating 5-iodoindole, coupling it to trimethylsilylacetylene and desilylating:

5-iodo-1-methyl-1H-indole: 5-Iodoindole (4.8 g, 20 mmol) was stirred in dry DMF (20 ml) containing MeI (8.5 g, 60 mmol) and $K_2CO_3$ (13.8 g, 100 mmol) for overnight at 55° C. The reaction mixture was diluted with EtOAc and passed through celite plug. The illiterate was evaporated to dryness and then oil was further purified by small flash column, Yield (90%). $^1$H NMR (300 MHz, CDCl$_3$) δ: 3.75 (s, 3H, NMe), 6.39 (d, J=3.0, 1H), 6.98 (d, J=3.0, 1H), 7.07 (d, J=9.0, 1H), 7.44 (dd, J1=9.0, J2=1.2, 1H), 7.93 (d, J=1.2, 1H).

5-ethynyl-1-methyl-1H-indole: 5-iodo-1-methyl-1H-indole (1.5 g, 5.84 mmol) were dissolved in mixture of $CH_2Cl_2$ (10 ml) and NEt$_3$ (5 ml) and the system was evacuated-back filled by $N_2$ thrice. Pd(PPh$_3$)$_2$Cl$_2$ (122 mg, 3% mol) and TMS-acetylene (0.858 g, 8.7 mmol) were added to it and again flushed $N_2$ into the system. CuI (89 mg, 8% mol) was added and flushed $N_2$ very quickly and reaction was stirred under positive pressure of $N_2$ until reaction completed by TLC (ca. 3 hours). The reaction mixture was diluted with 10 ml of hexane and filtered through celite plug, purified by passing through small column and then suspended in MeOH (20 ml) containing 10 ml of THF. NaOH was added to reaction mixture and stirred at room temp until starting material consumed completely. The reaction mixture was concentrated to 10 ml and extracted with EtOAc from aqueous $NH_4Cl$ solution, which was purified by column chromatography; Yield (60%); $^1$H NMR (300 MHz, CDCl$_3$) δ: 3.03 (s, 1H), 3.73 (s, 3H, NMe), 6.45 (d, J=3.0 Hz, 1H), 7.05 (d, J=3.0 Hz, 1H), 7.23 (d, J=9.0 Hz, 1H), 7.33 (dd, J=9.0, 1.2 Hz, 1H), 7.80 (bs, 1H).

Example 5

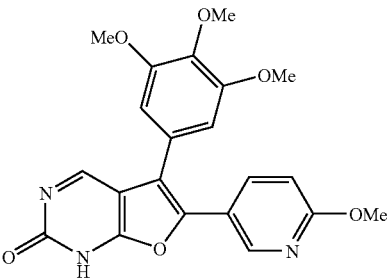 [SMILES: COc1ccc(-c2oc3[nH]c(=O)ncc3c2-c2cc(OC)c(OC)c(OC)c2)cn1]

6-(6-methoxypyridin-3-yl)-5-(3,4,5-trimethoxyphenyl)furo[2,3-d]pyrimidin-2(1H)-one Prepared According to General Procedure 1:

Step 1: 5-Iodouracil was coupled to 4-ethynyl-2-methoxypyridine. After quenching the reaction with MeOH, the solid separated was filtered and washed thoroughly with mixture of Et$_2$O and MeOH. $^1$H NMR (300 MHz, DMSO-d6) δ: 3.84 (s, 3H, OMe), 6.83 (d, J=8.7 Hz, 1H), 7.73 (dd, J=7.8, 1.3 Hz, 1H), 7.85 (s, 1H), 8.26 (d, J=1.3 Hz, 1H), 11.28 (bs, 1H, NH), 11.38 (bs, 1H, NH).

Step 2: The product from step 1 was coupled to 3,4,5-trimethoxyiodobenzene. The residue was purified by silica gel column chromatography using $CH_2Cl_2$, increasing gradient of EtOAc (to 1:1 mixture) and then 5% MeOH in 1:1 mixture of EtOAc and $CH_2Cl_2$ as eluant. The isolated creamy semi-solid gum was further purified by precipitating from mixture of Et$_2$O and EtOAc; Yield (62%). $^1$H NMR (300 MHz, DMSO-d6) δ: 3.69 (s, 9H, 3×OMe), 3.84 (s, 3H, OMe), 6.72 (s, 2H), 6.86 (d, J=8.7 Hz, 1H), 7.75 (dd, J=7.8, 2.4 Hz, 1H), 8.24 (s, 1H), 8.33 (d, J=2.4 Hz, 1H), 11.28 (bs, 1H, NH), 11.38 (bs, 1H, NH).

Example 6

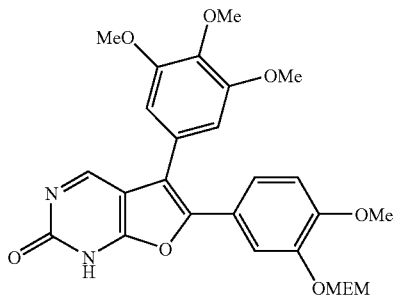

6-[4-Methoxy-3-(2-methoxy-ethoxymethoxy)-phenyl]-5-(3,4,5-trimethoxyphenyl)-1H-furo[2,3-d]pyrimidin-2-one Prepared According to General Procedure 1:

Step 1: 5-Iodouracil was coupled to MEM protected 5-ethynyl-2-methoxyphenol (Organic & Biomolecular Chemistry (2005), 3(14), 2657-2660). The brownish residue was purified by silica gel column chromatography using 40% EtOAc to pure EtOAc. Yield (65%); $^1$H NMR (300 MHz, DMSO-d6) δ: 3.19 (s, 3H, OMe), 3.43 (AA'BB', 2H, OCH$_2$), 3.70 (AA'BB', 2H, OCH$_2$), 3.76 (s, 3H, OMe), 5.20 (s, 2H, OCH$_2$O), 6.96 (d, J=8.7 Hz, 1H), 7.13 (d, J=8.7 Hz, 1H), 7.10 (s, 1H), 7.82 (s, 1H), 11.30 (bs, 1H, NH), 11.37 (bs, 1H, NH).

Step 2: The product from step 1 was coupled to 3,4,5-trimethoxyiodobenzene. The residue was precipitated from CH$_2$Cl$_2$ by slow addition of MeOH and then concentrating the mixture under vacuum without heating. The white creamy solid was filtered and dried. Yield (60%); $^1$H NMR (300 MHz, CDCl$_3$) δ: 3.33 (s, 3H, OMe), 3.49 (AA'BB', 2H, OCH$_2$), 3.78 (AA'BB', 2H, OCH$_2$), 3.80 (s, 6H, 2×OMe), 3.87 (s, 3H, OMe), 3.91 (s, 3H, OMe), 5.17 (s, 2H, OCH$_2$O), 6.61 (s, 2H), 6.83 (d, J=8.7 Hz, 1H), 7.29 (dd, J=8.7, 2.0 Hz, 1H), 7.44 (d, J=2.0 Hz, 1H), 8.01 (s, 1H).

Example 7

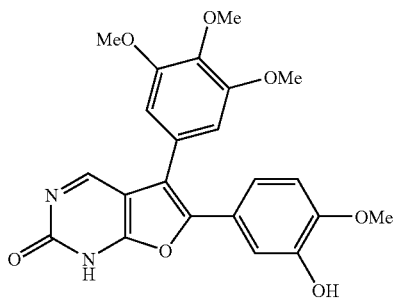 [SMILES: COc1ccc(-c2oc3[nH]c(=O)ncc3c2-c2cc(OC)c(OC)c(OC)c2)cc1O]

6-(3-Hydroxy-4-methoxy-phenyl)-5-(3,4,5-trimethoxy-phenyl)-1H-furo[2,3-d]pyrimidinone 6-[4-Methoxy-3-(2-methoxy-ethoxymethoxy)-phenyl]-5-(3,4,5-trimethoxyphenyl)-1H-furo[2,3-d]pyrimidin-2-one (Example 6) (102 mg, 0.2 mmol) was dissolved in mixture of THF (2 ml) and MeOH (2 ml) and 0.2 ml of concentrated HCl was added slowly with stirring. The reaction mixture was stirred for overnight with slow evaporation of solvents. The residue was dissolved in EtOAc (50 ml) and washed with water (5 ml). The organic layer was concentrated and purified by silica gel column chromatography using increasing gradient of EtOAc in CH$_2$Cl$_2$ and finally with 5% MeOH in 1:1 mixture of EtOAc and CH$_2$Cl$_2$. Yield (42%); $^1$H NMR (300 MHz, DMSO-d6) δ: 3.69 (s, 9H, 3×OMe), 3.75 (s, 3H, OMe), 6.71 (s, 2H), 6.92-7.11 (m, 3H), 8.15 (s, 1H).

Example 8

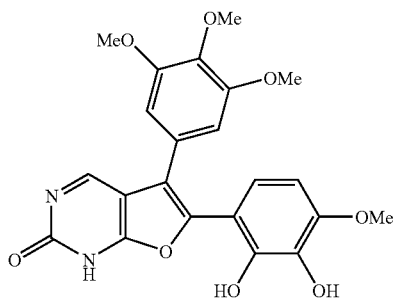 [SMILES: COc1ccc(-c2oc3[nH]c(=O)ncc3c2-c2cc(OC)c(OC)c(OC)c2)c(O)c1O]

6-(2,3-Dihydroxy-4-methoxy-phenyl)-5-(3,4,5-trimethoxy-phenyl)-1H-furo[2,3-d]pyrimidin-2-one Prepared According to General Procedure 1:

Step 1: 5-Iodouracil was coupled to bis-MOM protected 5-ethynyl-2-methoxycatechol. The residue was precipitated from CH$_2$Cl$_2$ by slow addition of MeOH and then concentrating the mixture under vacuum without heating. The white creamy solid was filtered and dried. Yield (50%); $^1$H NMR (300 MHz, DMSO-d6) δ: 3.44 (s, 3H, OMe), 3.48 (s, 3H, OMe), 3.78 (s, 3H, OMe), 5.00 (s, 2H, OCH$_2$O), 5.19 (s, 2H, OCH$_2$O), 6.82 (d, J=8.7, 1H), 7.13 (d, J=8.7, 1H), 7.77 (s, 1H), 11.26 (bs, 1H), 11.34 (bs, 1H).

Step 2: The product from step 1 was coupled with 3,4,5-trimethoxyiodobenzene and the crude material eluted through short plug silica gel with EtOAc (1 cm×1 cm) and the eluant concentrated. The product was dissolved in mixture of THF (3 ml) and MeOH (2 ml) and 0.2 ml of concentrated HCl was added slowly with stirring. The reaction mixture was stirred for overnight with slow evaporation of solvents. The residue was dissolved in EtOAc (50 ml) and washed with water (5 ml). The organic layer was concentrated and purified by silica gel column chromatography using increasing gradient of EtOAc in CH$_2$Cl$_2$ and finally with 5% MeOH in 1:1 mixture of EtOAc and CH$_2$Cl$_2$. $^1$H NMR (300 MHZ, DMSO-d6) δ: 3.61 (s, 9H, 3×OMe), 3.77 (s, 3H, OMe), 6.52 (d, J=8.7 Hz, 1H), 6.60 (s, 2H), 6.67 (d, J=8.7 Hz, 1H), 8.37 (s, 1H), 8.77 (s, 1H, OH), 8.96 (s, 1H, OH).

Example 9

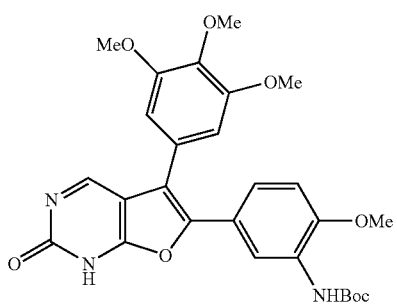

{2-Methoxy-5-[2-oxo-5-(3,4,5-trimethoxy-phenyl)-1,2-dihydro-furo[2,3-d]pyrimidin-6-yl]-phenyl}-carbamic acid tert-butyl ester Prepared According to General Procedure 1:

Step 1: 5-Iodouracil was coupled to Boc-protected protected 5-ethynyl-2-methoxyaniline. After quenching the reaction mixture with MeOH, the product was isolated by silica gel chromatography using increasing gradient of EtOAc in dichloromethane as off-white solid, yield (45%). $^1$H NMR (300 MHz, DMSO-d6) δ: 1.42 (s, 9H, t-Bu), 3.79 (s, 3H, OMe), 6.96-6.99 (m, 2H), 7.73 (d, J=7.8 Hz, 1H), 7.82 (s, 1H), 8.00 (s, 1H), 11.28 (bs, 1H, NH), 11.36 (bs, 1H, NH).

Step 2: The product from step 1 was coupled to 3,4,5-trimethoxyiodobenzene. The product was isolated by column chromatography using increasing gradient of EtOAc in dichloromethane as white solid (65%). $^1$H NMR (300 MHz, DMSO-d6) δ: 1.42 (s, 9H, t-Bu), 3.61 (s, 3H, OMe), 3.68 (s, 3H, OMe), 3.70 (s, 6H, 2×OMe), 6.74 (s, 2H), 7.03 (s, 1H), 7.13 (d, J=7.8 Hz, 1H), 7.75 (d, J=7.8 Hz, 1H), 8.04 (s, 1H), 8.19 (s, 1H), 12.21 (bs, 1H).

Example 10

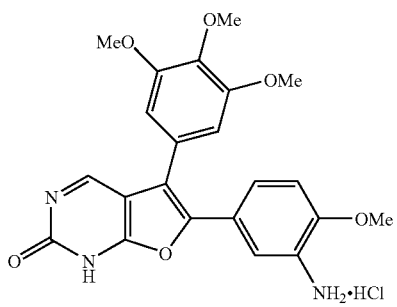

6-(3-amino-4-methoxyphenyl)-5-(3-hydroxy-4,5-dimethoxyphenyl)furo[2,3-d]pyrimidin-2(1H)-one hydrochloride The product of example 9: (52.3 mg, 1.0 mmol) was dissolved in neat TFA (5 ml) at 0° C. and the reaction temp was slowly raised to room temp and then stirred at room temp for 15 min. The solvents removed under vacuum and residue was dissolved in MeOH (4 ml) and few drops of concentrated HCl were added to it. The solvents were removed under vacuum and the oily residue was freeze-dried under high vacuum to yield the required hydrochloride salt as yellow powder. $^1$H NMR (300 MHz, DMSO-d6) δ: 3.63 (s, 3H, OMe), 3.67 (s, 3H, OMe), 3.70 (s, 6H, 2×OMe), 6.73 (s, 2H), 6.92 (d, J=7.8, 1H), 7.00 (s, 1H), 7.06 (d, J=7.8, 1H), 8.15 (s, 1H). LC-MS: 424.1 (M+H)$^+$.

Example 11

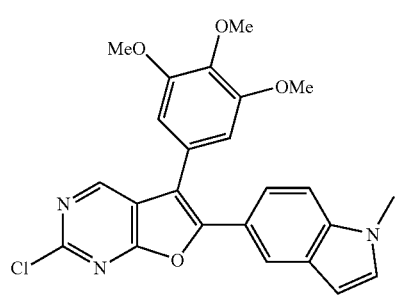 [SMILES: COc1cc(-c2c(-c3ccc4c(ccn4C)c3)oc3nc(Cl)ncc23)cc(OC)c1OC]

2-Chloro-6-(1-methyl-1H-indol-5-yl)-5-(3,4,5-trimethoxy-phenyl)-furo[2,3-d]pyrimidine The product of example 4 (200 mg, 0.46 mmol) was heated in freshly distilled P(O)Cl$_3$ (10 ml) to 90° C. for 3 hours and then solvents were removed under vacuum. The residue was dissolved in CH$_2$Cl$_2$ and washed with aqueous NaHCO$_3$ and evaporated. The residue was purified by silica gel column chromatography using increasing gradient of CH$_2$Cl$_2$ in hexane to pure CH$_2$Cl$_2$. Yield (40%); $^1$H NMR (300 MHz, CDCl$_3$) δ: 3.77 (s, 6H, 2×OMe), 3.79 (s, 3H, OMe), 3.94 (s, 3H, OMe), 6.49 (d, J=3.0 Hz, 1H), 6.71 (s, 2H), 7.08 (d, J=3.0 Hz, 1H), 7.27 (d, J=9.0 Hz, 1H), 7.53 (dd, J=9.0, 1.2 Hz, 1H), 8.05 (d, J=1.2 Hz, 1H), 8.72 (bs, 1H).

Example 12

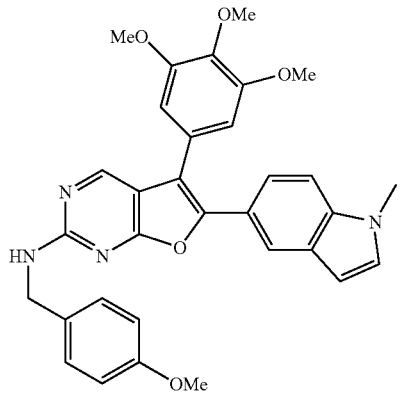 [SMILES: COc1ccc(CNc2ncc3c(-c4cc(OC)c(OC)c(OC)c4)c(-c4ccc5c(ccn5C)c4)oc3n2)cc1]

2-(4-methoxybenzamino)-6-(1-methyl-1H-indol-5-yl)-5-(3,4,5-trimethoxy-phenyl)-furo[2,3-d]pyrimidine The product of example 11 (50 mg) was dissolved in 0.4 ml of dry CH$_2$Cl$_2$ and THF (0.4 ml) was added to it. The reaction mixture was heated at 60-70° C. for 4 h under N$_2$ and then again 0.4 ml of dry CH$_2$Cl$_2$ was added to it. The reaction mixture heated overnight at 60-70° C. under N$_2$ atmosphere. The solvents were removed under vacuum and the residue was suspended in dry ether and sonicated. The white solid was further purified by small column yield (75%); $^1$H NMR (300 MHz, CDCl$_3$) δ: 3.75 (s, 6H, 2×OMe), 3.77 (s, 6H, 2×OMe), 3.93 (s, 3H, OMe), 4.65 (d, J=5.7 Hz, 2H), 5.63 (bt, J=5.7 Hz, 1H), 6.45 (d, J=3.0 Hz, 1H), 6.72 (s, 2H), 6.85 (d, J=8.7 Hz, 2H), 7.03 (d, J=3.0 Hz, 1H), 7.19 (d, J=8.7 Hz, 1H), 7.31 (d, J=8.7 Hz, 2H), 7.50 (dd, J=8.7, 1.2 Hz, 1H), 8.11 (d, J=1.2 Hz, 1H), 8.46 (s, 1H).

Example 13

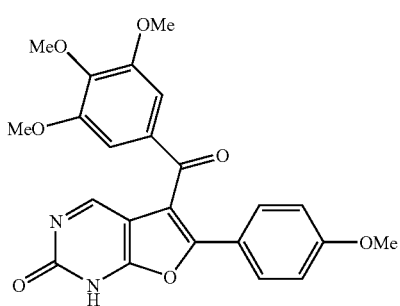 [SMILES: COc1ccc(-c2oc3[nH]c(=O)ncc3c2C(=O)c2cc(OC)c(OC)c(OC)c2)cc1]

Prepared according to the procedure described for example 1 except the N$_2$ gas was replaced with CO(g) in step 2. The crude material was purified by p.t.l.c, 2% MeOH, 98% CH$_2$Cl$_2$ white solid, 10 mg, 22%) $^1$H NMR (300 MHz, CDCl$_3$): δ 9.87 (br s, 1H), 7.53 (d, J=4.5 Hz, 1H), 7.41 (d, J=7.8 Hz, 2H), 7.19 (s, 2H), 6.84 (d, J=7.8 Hz, 2H), 3.94 (s, 3H), 3.89 (s, 6H), 3.80 (s, 3H). MS (ESI, 437 [M+H]$^+$).

Example 14

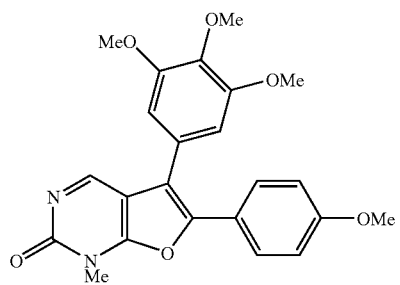 [SMILES: COc1ccc(-c2oc3c(cnc(=O)n3C)c2-c2cc(OC)c(OC)c(OC)c2)cc1]

A mixture of example 1 (25 mg, 0.065 mmol), K$_2$CO$_3$ (25 mg, 0.18 mmol) and MeI (87 mg, 0.61 mmol) in DMF (1.0 mL) was stirred at room temperature for 16 hours. The mixture was diluted with ethyl acetate, washed with H$_2$O (2×), dried (MgSO$_4$), filtered and concentrated. The residue was purified by p.t.l.c (2:1 ethyl acetate/acetone) to give the N-methylated product (5 mg, 20%). $^1$H NMR (300 MHz, CDCl$_3$): δ 7.73 (s, 1H), 7.54 (d, J=8.9 Hz, 2H), 6.83 (d, J=8.9 Hz, 2H), 6.58 (s, 2H), 3.91 (s, 3H), 3.80 (s, 9H), 3.64 (s, 3H). $^{13}$C (75 MHz, CDCl$_3$) δ 170.41, 160.17, 155.67, 153.70, 149.30, 139.08, 137.92, 128.07, 125.57, 120.61, 113.70, 111.66, 110.17, 105.90, 60.63, 56.02, 54.97, 39.54.

Example 15

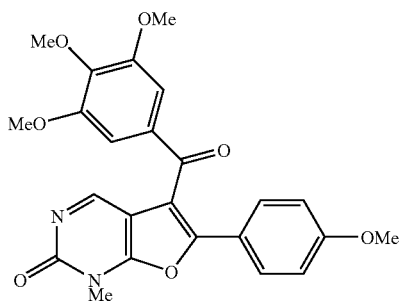

Prepared according to the procedure described for example 14 starting with the product of example 13, purified by ptlc (1% NEt$_3$, 2% MeOH, 97% CH$_2$Cl$_2$), yield=25%. $^1$H NMR (300 MHz, CDCl$_3$): δ 7.56 (s, 1H), 7.39 (d, J=8.8 Hz, 2H), 7.15 (s, 2H), 6.82 (d, J=8.8 Hz, 2H), 3.91 (s, 3H), 3.87 (s, 6H), 3.78 (s, 3H), 3.45 (s, 3H).

Example 16

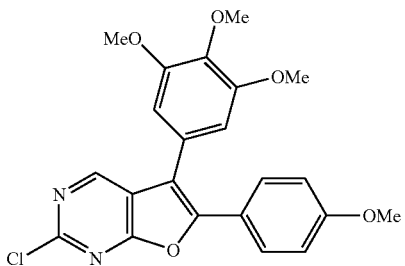 [SMILES: COc1ccc(-c2oc3nc(Cl)ncc3c2-c2cc(OC)c(OC)c(OC)c2)cc1]

2-Chloro-6-(4-methoxyphenyl)-5-(3,4,5-trimethoxyphenyl)-furo[2,3-d]pyrimidine

A stirred mixture of example 1 and P(O)Cl$_3$ was heated at 100° C. for 3 hours. The mixture was then poured onto ice-water, and extracted with Et$_2$O (3×). The combined ethereal extracts were dried (MgSO$_4$), filtered and concentrated. The residue was purified by ptlc (1% NEt$_3$, 1% MeOH, 98% CH$_2$Cl$_2$) providing 10 mg (47%) of desired product. $^1$H NMR (300 MHz, CDCl$_3$): δ 8.71 (s, 1H), 7.65 (d, J=8.9 Hz, 2H), 6.88 (d, J=8.9 Hz, 2H), 6.65 (s, 2H), 3.93 (s, 3H), 3.83 (s, 3H), 3.80 (s, 6H).

Example 17

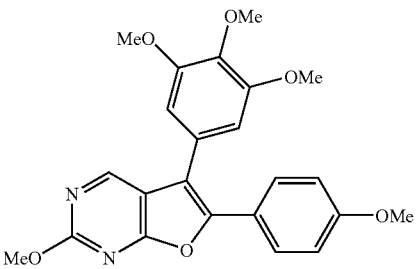 [SMILES: COc1ccc(-c2oc3nc(OC)ncc3c2-c2cc(OC)c(OC)c(OC)c2)cc1]

2-Methoxy-6-(4-methoxyphenyl)-5-(3,4,5-trimethoxyphenyl)-furo[2,3-d]pyrimidine

Sodium (50 mg, 2.17 mmol) was added portionwise to MeOH (8 mL). Once all the metal had dissolved example 16

(50 mg, 0.12 mmol) was added and the mixture heated to reflux for 2 hours. The mixture was allowed to cool, then diluted with H$_2$O, and washed with Et$_2$O (3×). The combined ethereal extracts were dried (MgSO$_4$), filtered and concentrated. The residue was purified by p.t.l.c (1% NEt$_3$, 2% MeOH, 97% CH$_2$Cl$_2$) providing 20 mg (40%) of desired product. $^1$H NMR (300 MHz, CDCl$_3$): δ 8.64 (s, 1H), 7.63 (d, J=8.9 Hz, 2H), 6.87 (d, J=8.9 Hz, 2H), 6.67 (s, 2H), 4.09 (s, 3H), 3.92 (s, 3H), 3.82 (s, 3H), 3.79 (s, 6H).

Example 18

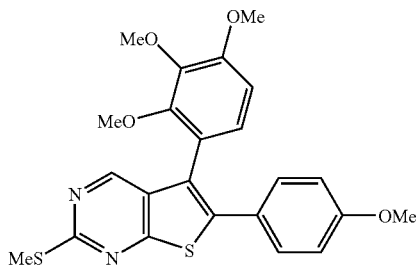 [SMILES: COc1ccc(-c2sc3nc(SC)ncc3c2-c2ccc(OC)c(OC)c2OC)cc1]

2-Thiomethoxy-6-(4-methoxyphenyl)-5-(3,4,5-trimethoxybenzoyl)-thiopheno [2,3-d]pyrimidine This material was prepared through the following sequence steps:

67%). $^1$H NMR (300 MHz, CDCl$_3$) δ 8.79 (br s, 1H), 7.63 (d, J=8.7 Hz, 2H), 7.03 (d, J=8.7 Hz, 2H), 3.89 (s, 3H), 2.70 (s, 3H).

C: A stirred mixture of B (100 mg, 0.24 mmol), hexamethylditin (79 mg, 0.24 mmol) and Pd(PPh$_3$)$_2$Cl$_2$ (10 mg, 12 μmol) in toluene (3 mL, dry) under nitrogen was heated at 90° C. for 6 hours. The mixture was diluted with Et$_2$O and washed with H$_2$O (2×) and brine, dried (MgSO$_4$), filtered and concentrated. The residue was purified by fcc (1:9 EtOAc, hexane) providing 60 mg (55%) of stannylated material C. $^1$H NMR (300 MHz, CDCl$_3$): δ 8.87 (s, 1H), 7.37 (d, J=8.7 Hz, 2H), 6.97 (d, J=8.7 Hz, 2H), 3.88 (s, 3H), 2.66 (s, 3H), 0.24 (s, 9H).

D: A mixture of Pd$_2$dba$_3$ (9.5 mg, 17 μmol) and PPh$_3$ (17.5 mg, 67 μmol) in THF (8 mL) was stirred for 15 minutes at room temperature. 3,4,5-trimethoxybenzoyl chloride (75 mg, 0.32 mmol), C (150 mg, 0.33 mmol) and CuCl (27 mg, 0.27 mmol) were added and the mixture left to stir at room temperature overnight. The mixture was diluted with ethyl acetate and washed with H$_2$O (2×) and brine then dried (MgSO$_4$), filtered and concentrated. The residue purified by fcc (1:3 EtOAc, hexane) providing 81 mg (27%) of coupled material. $^1$H NMR (300 MHz, CDCl$_3$): δ 8.89 (s, 1H), 7.31 (d, J=8.7 Hz, 2H), 7.01 (s, 2H), 6.78 (d, J=8.7 Hz, 2H), 3.84 (s, 3H), 3.76 (s, 3H), 3.74 (s, 6H), 2.67 (s, 3H). MS (ESI, 483 [M+H]$^+$).

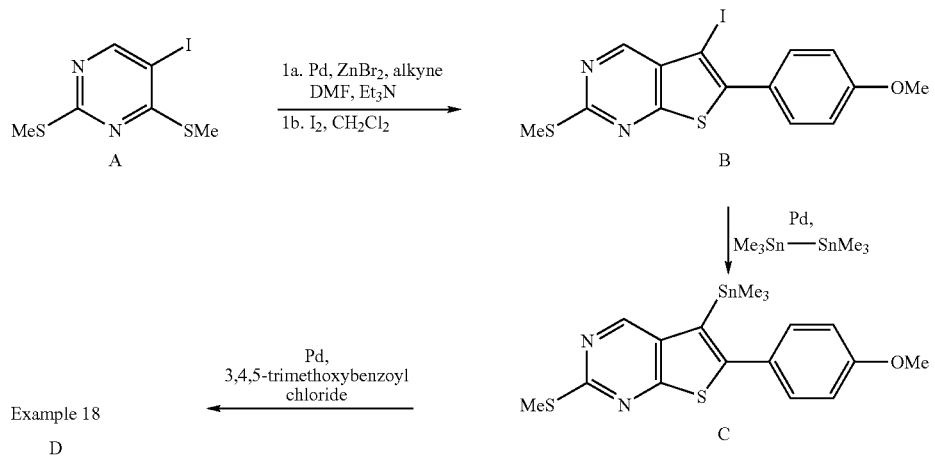

B: To a stirred mixture of 2,6-thiomethoxy-5-iodopyrimidine (A, prepared by reaction of 2.2 equivalents MeSNa with 2,6-dichloro-5-iodopyrimidine in DMF) (1.0 g, 3.36 mmol), Pd(PPh$_3$)$_2$Cl$_2$ (82 mg, 0.11 mmol), ZnBr$_2$ (0.76 g, 3.36 mmol) and NEt$_3$ (1.0 g, 9.9 mmol) in DMF (4 mL) was added 1-ethynyl-4-methoxybenzene (0.28 g, 4.18 mmol). The mixture was heated at 75° C. for one hour, allowed to cool to room temperature then diluted with CH$_2$Cl$_2$. The mixture was then washed with H$_2$O (3×), aqueous sodium metabisulphite solution (5%), dried (MgSO$_4$), filtered and concentrated to give the desired coupled material. The residue was taken up in CH$_2$Cl$_2$ (50 mL), iodine (1.01 g, 3.97 mmol) added and the mixture stirred at room temperature for one hour. The mixture was washed with sodium thiosulphate solution (10%, 2×), brine, then dried (MgSO$_4$), filtered and concentrated to give the desired cyclised material B, as a pale yellow solid (0.93 g, Example 19

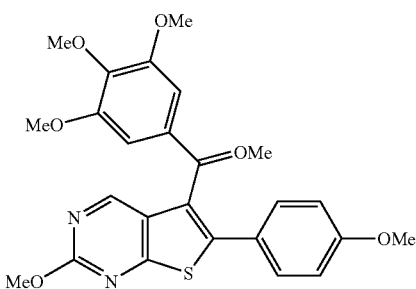

2-Methoxy-6-(4-methoxyphenyl)-5-(3,4,5-tri-methoxybenzoyl)-thiopheno[2,3-d]pyrimidine As with example 17 but using example 18 in place of example 16, purified by ptlc (1:2 ethyl acetate/hexane), 15 mg (79%). ¹H NMR (300 MHz, CDCl₃): δ 8.91 (s, 1H), 7.28 (d, J=8.7 Hz, 2H), 7.00 (s, 2H), 6.75 (d, J=8.7 Hz, 2H), 4.10 (s, 3H), 3.82 (s, 3H), 3.74 (s, 3H), 3.72 (s, 6H).

Examples 20 and 21

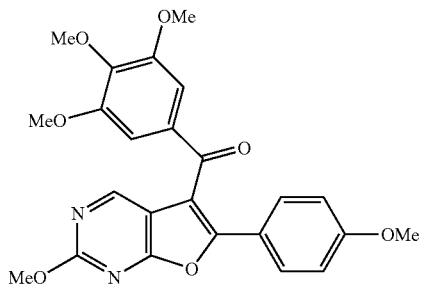
Example 20

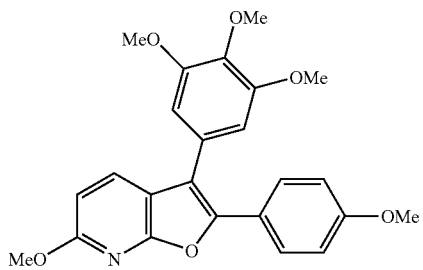
Example 21

6-methoxy-2-(4-methoxyphenyl)-3-(3,4,5-tri-methoxybenzoyl)furo[2,3-b]pyridine (Example 20) and 6-methoxy-2-(4-methoxyphenyl)-3-(3,4,5-tri-methoxyphenyl)furo[2,3-b]pyridine (Example 21)

These examples were prepared according to the following reaction sequence:

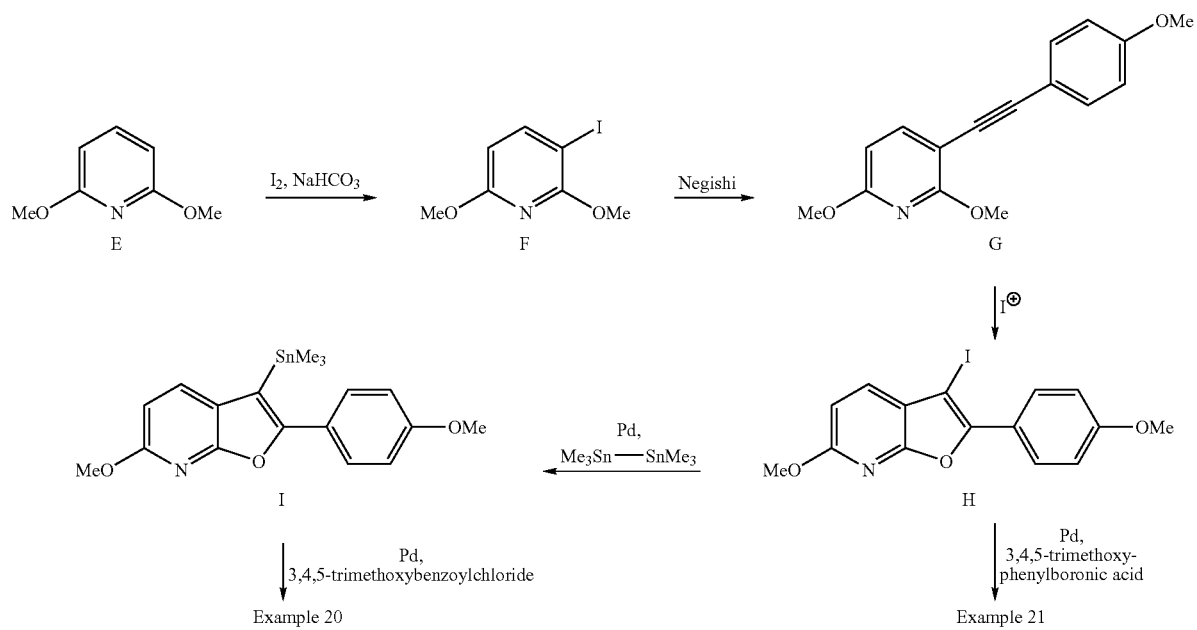

F: A mixture of 0.14 g (1 mmol) of 2,6-dimethoxypyridine E, 0.76 g (3 mmol) of iodine and 0.25 g (3 mmol) of sodium hydrogen carbonate was stirred overnight at room temperature. The resulting mixture was diluted to 40 ml with dichloromethane, washed with 10 ml of saturated aqueous sodium metabisulphite, 20 ml of saturated aqueous sodium hydrogen carbonate and dried over anhydrous magnesium sulfate. The filtration of drying agent, evaporation of the solvent and purification by flash column chromatography (silica gel, hexane: dichloromethane 9:1 gave 0.107 g (41% yield) of pure F as a colorless solid. ¹H NMR (300 MHz, CDCl₃): δ 7.77 (d, J=8.3 Hz, 1H), 6.11 (d, J=8.3 Hz, 1H), 3.94 (s, 3H); 3.88 (s, 3H);

G: n-Butyllithium (2M in cyclohexane; 3.5 ml, 6.93 mmol) was added dropwise to a solution of 1.008 g (3.44 mmol) of 4-methoxy-β,β-dibromostyrene in 5 ml of anhydrous tetrahydrofuran during 10 minutes at −78° C. under dry nitrogen atmosphere. After the addition was completed the reaction mixture was allowed to warm to ~50° C. and 0.78 g (3.46 mmol) of dry zinc bromide in 2 ml of anhydrous tetrahydrofuran was added under nitrogen. The resulting mixture was allowed to warm to room temperature. 41 ml of above mixture was added to a solution of F 0.1089 g (0.41 mmol) in 2 ml of anhydrous dimethyl formamide containing 0.025 g (0.036 mmol) of dichlorobis(triphenylphosphine)palladium under dry nitrogen atmosphere. The resulting mixture was stirred at 100° C. with a flow of nitrogen to remove tetrahydrofuran. The progress of the reaction was monitored by TLC and the reaction was completed in 1 h. The resulting mixture was diluted to 50 ml with dichloromethane, washed with saturated aqueous solution of ammonium chloride (20 ml) and brine. The organic phase was dried over anhydrous magnesium sulfate and filtered. Evaporation of the filtrate and purification by flash column chromatography gave 0.0997 g (90% yield) of pure G as a colorless crystals. ¹H NMR (300 MHz, CDCl₃):

δ 7.61 (d, J=6.0 Hz, 1H) 7.43 (d, J=8.7 Hz, 2H); 6.84 (d, J=8.7 Hz, 2H); 6.28 (d, J=6.0 Hz, 1H); 4.0 (s, 3H); 3.91 (s, 3H); 3.80 (s, 3H);

H: A mixture of 0.1082 g (0.4 mmol) of above product G and 0.21 g (0.44 mmol) of iodonium bis(syn-collidine) perchlorate in 3 ml of anhydrous tetrahydrofuran was refluxed for 10 minutes, than diluted to 30 ml with dichloromethane, washed with saturated sodium metabisulphite (10 ml), saturated sodium hydrogen carbonate (10 ml), dried over anhydrous magnesium sulphate and filtered. Evaporation of the filtrate and purification of the residue by flash column chromatography (silica gel, hexane:ethyl acetate, 9:1) gave 0.031 g (20.2% yield) of pure H as a colorless solid. $^1$H NMR (300 MHz, CDCl$_3$): δ 8.11 (d, J=8.7 Hz, 2H), 7.60 (d, J=8.4 Hz, 1H), 7.01 (d, J=8.7 Hz, 2H), 6.75 (d, J=8.4 Hz, 1H), 4.03 (s, 3H), 3.88 (s, 3H).

I: A stirred mixture of H (110 mg, 0.29 mmol), hexamethylditin (95 mg, 0.29 mmol) and Pd(PPh$_3$)$_2$Cl$_2$ (12 mg, 17 μmol) in toluene (5 mL, dry) under nitrogen was heated at reflux for 2 hours. The mixture was diluted with Et$_2$O and washed with H$_2$O (2×) and brine, dried (MgSO$_4$), filtered and concentrated. The residue purified by p.t.l.c (1:20 EtOAc, hexane) providing 50 mg (42%) of stannylated material I. $^1$H NMR (300 MHz, CDCl$_3$): δ 7.75 (d, J=8.4 Hz, 1H), 7.62 (d, J=11.2 Hz, 2H), 6.96 (d, J=11.2 Hz, 2H), 6.67 (d, J=8.4 Hz, 1H), 4.02 (s, 3H), 3.87 (s, 3H), 0.36 (s, 9H).

Example 20

A mixture of Pd$_2$dba$_3$ (4 mg, 7 μmol) and PPh$_3$ (7.5 mg, 29 μmol) in THF (2 mL) was stirred for 15 minutes at room temperature. 3,4,5-trimethoxybenzoyl chloride (40 mg, 0.17 mmol), S (60 mg, 0.14 mmol) and CuCl (11 mg, 0.12 mmol) were added and the mixture left to stir at room temperature overnight. The mixture was diluted with ethyl acetate and washed with H$_2$O (2×) and brine then dried (MgSO$_4$), filtered and concentrated. The residue was purified by p.t.l.c (1:3 EtOAc, hexane) providing 17 mg (27%) of coupled material. $^1$H NMR (300 MHz, CDCl$_3$): δ 7.87 (d, J=8.4 Hz, 1H), 7.60 (d, J=9.0 Hz, 2H), 7.11 (s, 2H), 6.82 (d, J=9.0 Hz, 2H), 6.77 (d, J=8.4 Hz, 1H), 4.05 (s, 3H), 3.88 (s, 3H), 3.80 (s, 3H), 3.70 (s, 6H).

Example 21

To a mixture of 0.0306 g (0.0787 mmol) of H, 0.0332 g (0.173 mmol) of 3,4,5-trimethoxyphenylboronic acid, 0.009 g (0.0077 mmol) of tetrakis(triphenylphosphine)palladium (0) in 3 ml of anhydrous dioxane, a solution of 0.033 mg (0.39 mmol) of sodium hydrogen carbonate in 1 ml of water was added at reflux under nitrogen atmosphere. After 3 minutes of stirring at reflux the reaction mixture was evaporated to dryness under reduced pressure and the residue was purified by flash column chromatography (silica gel, methylene chloride) to give 0.031 mg (99% yield) of pure product as a creamy solid. $^1$H NMR (300 MHz, CDCl$_3$): δ 7.7 (d, J=8.4 Hz, 1H); 7.62 (d, J=6.9 Hz, 2H); 6.84 (d, J=6.9 Hz, 2H); 6.6-6.72 (m, 3H); 3.81 (3×s, 9H).

Example 22 and Example 23

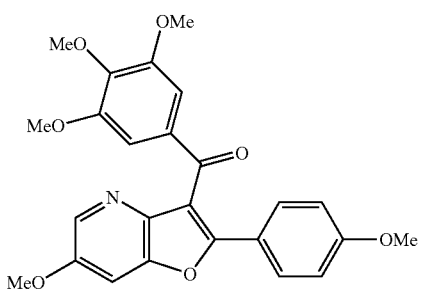

Example 22

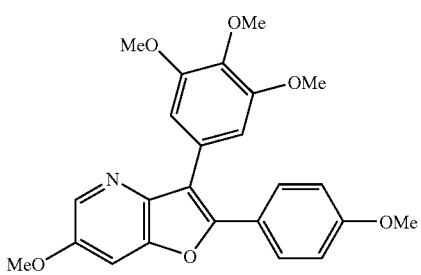

Example 23

6-methoxy-2-(4-methoxyphenyl)-3-(3,4,5-trimethoxybenzoyl)furo [3,2-b]pyridine (Example 22) and 6-methoxy-2-(4-methoxyphenyl)-3-(3,4,5-trimethoxyphenyl)furo[3,2-b]pyridine (Example 23)

These two examples were prepared according to the following reaction sequence:

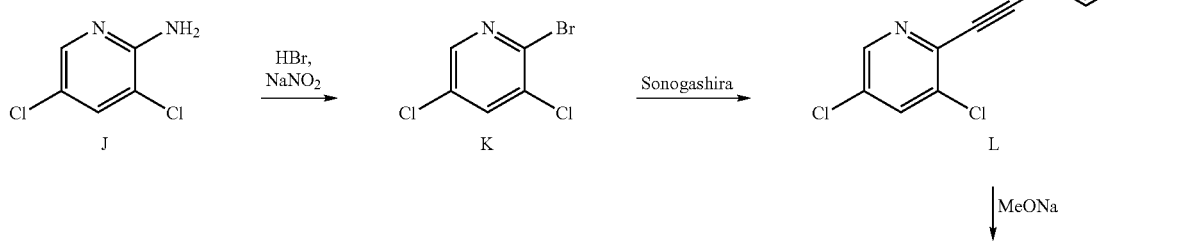

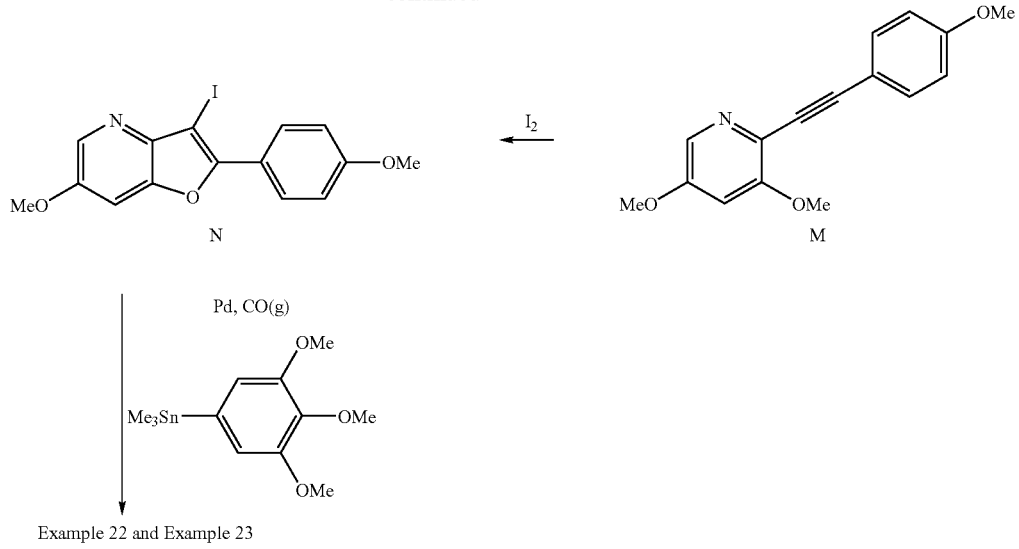

Example 22 and Example 23

K: 2-Amino-3,5-dichloropyridine J (10 g, 61.3 mmol) was dissolved in an aqueous HBr solution (100 mL 48% HBr, 200 mL $H_2O$), then cooled to 0° C. $Br_2$ (10 mL) was added in one portion, followed by the dropwise addition of $NaNO_2$ solution (6.35 g, 92.0 mmol, 15 mL $H_2O$). The mixture was stirred at 0° C. for 30 minutes, then allowed to warm to room temperature before being heated to 70° C. for 30 minutes. The cooled mixture was then neutralised with KOH solution (5.0 M) then extracted with ethyl acetate (3×200 mL), dried ($MgSO_4$), filtered and concentrated. The residue was purified by chromatography (1:4 EtOAc, hexane) providing 8.2 g (59%) of K as a yellow crystalline solid. $^1$H NMR (300 MHz, $CDCl_3$): δ 8.27 (d, J=2.1 Hz, 1H), 7.77 (d, J=2.1 Hz, 1H).

L: Nitrogen was bubbled through a mixture of 2-bromo-3,5-dichloropyridine K (6.2 g, 27.2 mmol), 1-ethynyl-4-methoxybenzene (3.58 g, 27.2 mmol) and $Pd(PPh_3)_2Cl_2$ (0.96 g, 1.36 mmol) in piperidine (100 mL) for 15 minutes. CuI (0.26 g, 1.36 mmol) was added and the nitrogen gas flow maintained for 1.5 hours as the reaction was stirred. The mixture was diluted with $Et_2O$ (250 mL) and washed with $H_2O$ (200 mL). The aqueous extract was then washed with $Et_2O$ (2×200 mL) and all the organic extracts combined. These were then washed with $H_2O$ (3×200 mL) and brine, dried ($MgSO_4$), filtered and concentrated. The residue was purified by chromatography (1:6 EtOAc, hexane) providing the coupled product L as an orange solid (5.3 g, 66%). $^1$H NMR (300 MHz, $CDCl_3$): δ 8.43 (d, J=2.2 Hz, 1H), 7.75 (d, J=2.2 Hz, 1H), 7.55 (d, J=8.7 Hz, 2H), 6.87 (d, J=8.7 Hz, 2H), 3.83 (s, 3H).

M: Sodium (0.50 g, 21.7 mmol) was added portionwise to methanol (15 mL) and the mixture stirred until all the sodium had disappeared. The solvent was removed under reduced pressure, then replaced with DMF (13 mL). To the stirred mixture was then added L (1.0 g, 3.60 mmol) and the resulting solution heated to 80° C. for 2 hours. The mixture was allowed to cool, then diluted with ethyl acetate (200 mL) and washed with $H_2O$. The aqueous phase was separated and extracted with ethyl acetate (2×150 mL). The organic extracts were combined, washed with $H_2O$ and brine, dried ($MgSO_4$), filtered and concentrated. The residue was purified by chromatography (1:1 ethyl acetate, hexane), providing 0.50 g (52%) of desired product M. $^1$H NMR (300 MHz, $CDCl_3$): δ 7.90 (d, J=2.4 Hz, 1H), 7.74 (d, J=2.4 Hz, 1H), 7.52 (d, J=8.9 Hz, 2H), 6.86 (d, J=8.9 Hz, 2H), 3.89 (s, 3H), 3.88 (s, 3H), 3.80 (s, 3H).

N: A stirred mixture of M (0.45 g, 1.67 mmol) and bis(pyridine)iodonium tetrafluoroborate (0.75 g, 2.00 mmol) in THF (20 mL) was heated at reflux for 15 minutes. The solvent was removed and the residue partitioned between ethyl acetate and aqueous sodium metabisulphite solution (5%). The organic extract was then washed with $H_2O$ and Brine, dried ($MgSO_4$), filtered and concentrated. The residue was purified by chromatography (2:3 ethyl acetate, hexane), providing 0.45 g (71%) of cyclised product N. $^1$H NMR (300 MHz, $CDCl_3$): δ 8.35 (d, J=2.4 Hz, 1H), 8.12 (d, J=9.0 Hz, 2H), 7.27 (d, J=2.4 Hz, 1H), 7.01 (d, J=9.0 Hz, 2H), 3.90 (s, 3H), 3.87 (s, 3H).

Example 22 and 23

A stirred mixture of N (0.10 g, 0.26 mmol), trimethyl(3,4,5-trimethoxyphenyl)stannane (0.10 g, 0.30 mmol) and $Pd(PPh_3)_4$ (15 mg, 13 μmol) in DMSO (4 mL) was heated to 100° C. overnight under an atmosphere of CO. The cooled reaction mixture was diluted with ethyl acetate and washed with $H_2O$ (2×) and brine, dried ($MgSO_4$), filtered and concentrated. The crude residue was purified by chromatography (2:3 ethyl acetate, hexane) giving pure samples of Example 22 (Rf=0.25, 49 mg, 41%) and Example 23 (Rf=0.35, 31 mg, 38%) of coupled product. Example 22: $^1$H NMR (300 MHz, $CDCl_3$): δ 8.30 (d, J=2.3 Hz, 1H), 7.69 (d, J=8.8 Hz, 2H), 7.36 (d, J=2.3 Hz, 1H), 7.24 (s, 2H), 6.88 (d, J=8.8 Hz, 2H), 3.91 (s, 3H), 3.89 (s, 3H), 3.80 (s, 3H), 3.73 (s, 6H). $^{13}$C($CDCl_3$, 75 MHz): δ 189.94, 161.04, 158.31, 154.10, 152.94, 147.27, 143.20, 140.66, 136.68, 132.14, 129.19, 121.72, 115.07, 114.20, 107.97, 102.95, 60.87, 56.33, 56.24, 55.35. MS (ESI, 450 [M+H]$^+$). Example 23: $^1$H NMR (300 MHz, $CDCl_3$): δ 8.32 (d, J=2.4 Hz, 1H), 7.64 (d, J=9.0 Hz, 2H), 7.35 (d, J=2.4 Hz, 1H), 6.88 (d, J=9.0 Hz, 2H), 6.82 (s, 2H), 3.92 (s, 3H), 3.89 (s, 3H), 3.82 (s, 3H), 3.80 (s, 6H).

Example 24

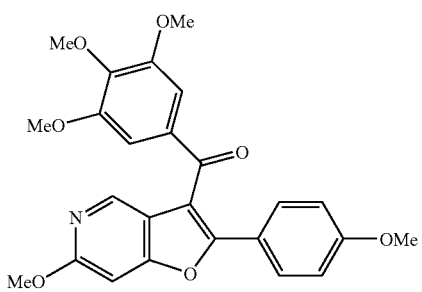

6-methoxy-2-(4-methoxyphenyl)-3-(3,4,5-tri-methoxybenzoyl)furo[3,2-c]pyridine

This compound was prepared according to the following reaction sequence:

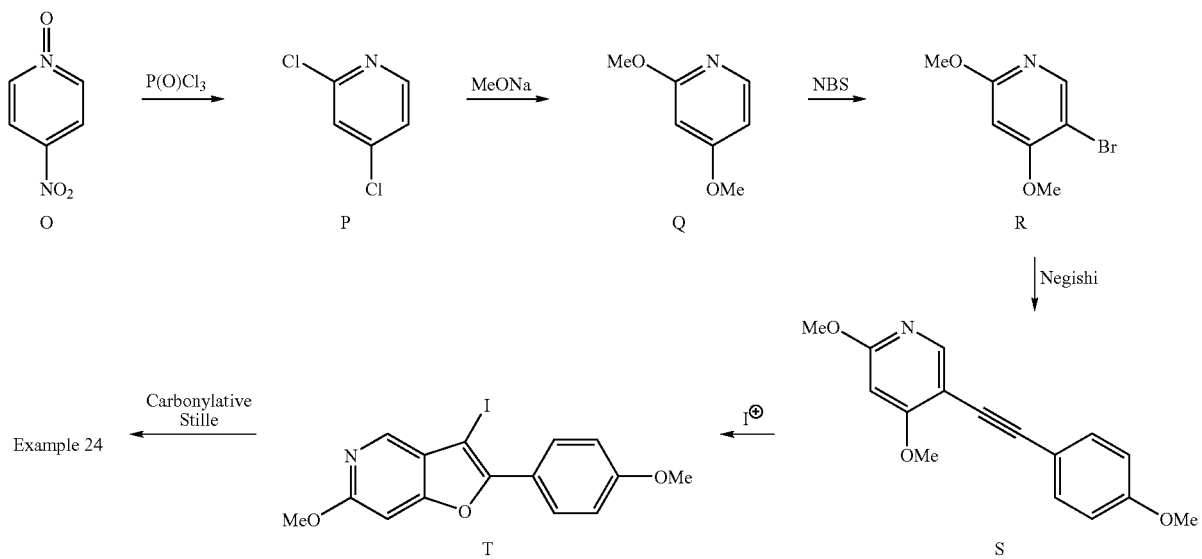

2,4-Dimethoxypyridine (Q): A mixture of 4-nitropyridine N-oxide O (21.6 g; 15.4 mmol) and P(O)Cl₃ (11.41 g; 21.5 mmol) was refluxed for 10 h then the excess of P(O)Cl₃ was removed under reduced pressure. The residue was treated with ice (10 g) and pH of resulting mixture was adjusted to ~5 with aqueous NaOH. This was extracted with diethyl ether (3×150 ml). The combined ether extracts were washed with brine, dried over anhydrous MgSO4 and evaporated to dryness to give 3.5 g (15%) of pure 2,4-dichloropyridine P as a slightly yellowish oil, after purification by column chromatography (silica gel; $CH_2Cl_2$) $^1$HNMR (CDCl₃) δ 8.28 (m, 1H); 7.36 (m, 1H); 7.22 (m, 1H). This was dissolved in anhydrous DMF (15 ml) containing freshly prepared sodium methoxide (2.81 g; 5.2 mmol). The resulting mixture was stirred overnight at 80° C. under anhydrous N₂, that cooled to room temperature diluted to 100 ml with diethyl ether and washed with water (20 ml, brine (3×20 ml) and dried over anhydrous MgSO₄. Filtration and evaporation of filtrate under reduced pressure gave crude product Q, which was used in next step without further purification. $^1$HNMR (CDCl₃) δ 7.92 (d, J=5.92 Hz, 1H); 6.43 (dd, J=2.16, 5.92 Hz, 1H); 6.15 (d, J=2.16 Hz, 1H); 3.88 (s, 3H); 3.76 (s, 3H).

5-Bromo-2,4-dimethoxypyridine (R): A mixture of Q (3.37 g; 2.42 mmol) and N-bromosuccinimide (4.27 g; 2.4 mmol) in anhydrous CH₃CN (120 ml) was stirred in dark for 12 h at 70-85° C. After cooling to room temperature the mixture was diluted to 70 ml with hexane/CH₂Cl₂ (50:20) mixture. The precipitated solid was removed by filtration and the filtrate was evaporated to dryness and purified by column chromatography to give pure title product R (2.4 g; 46%) as a colourless crystals $^1$HNMR (CDCl₃) δ 8.1 (s, 1H) 6.21 (s, 1H); 3.88 (s, 3H); 3.85 (s, 3H).

2,4-Dimethoxy-5-(4-methoxyphenylethynyl)pyridine (S): n-Butyllithium (0.89 ml of 2 M solution in cyclohexane) was added dropwise to a solution of 1-(2,2-dibromovinyl)-4-methoxybenzene (0.26 g; 0.89 mmol) in anhydrous THF (2.5 ml) at −78° C. under dry N₂. The resulting mixture was stirred for 30 min and to it anhydrous ZnBr₂ (0.205 g) in anhydrous THF was added under N₂. The resulting mixture was allowed to warm up to room temperature and added to a mixture of the product of R (0.15 g; 0.68 mmol) and Cl₂Pd(PPh₃)₂ (0.036 g; 0.051 mmol) in anhydrous DMF (3 ml) under N₂. The resulting mixture was stirred at 80-100° C. overnight, while THF was removed during the first 30 min, by slight flow of dry N₂. After cooling down to room temperature the mixture was diluted to 40 ml with CH₂Cl₂, washed with saturated NH₄Cl (20 ml), brine (20 ml) and dried over anhydrous MgSO4, filtered off and filtrate evaporated to dryness under reduced pressure. The residue was purified by column chromatography to S (0.101 g, 55%) as colourless solid. $^1$HNMR (CDCl₃) δ 8.16 (s, 1H); 7.45 (dd, J=8.9, 1.0 Hz, 2H); 6.85 (dd, J=8.9, 1.0, Hz, 2H); 3.93 (d, 1.0 Hz, 3H); 6.19 (s, 1H); 3.88 (d, J=1.0 Hz, 3H); 3.8 (d, J=1.0 Hz, 3H).

3-Iodo-6-methoxy-2-(4-methoxyphenyl)furo[3,2-c]pyridine (T): Compound S (0.019 g; 0.0705 mmol) and bis(pyridine)iodonium tetrafluoroborate (0.0524 g; 0.14 mmol) in THF (3 ml) was refluxed for 30 min., then diluted to 50 ml with ethyl acetate, washed with saturated Na₂S₂O₅ (3 ml), saturated NaHCO₃, dried over anhydrous MgSO₄, filtered off and filtrate evaporated to dryness under reduced pressure. The residue was purified by column chromatography (silica gel, CH₂Cl₂) to give pure T (0.0175 g; 65%) ¹HNMR (CDCl₃) δ 8.2 (s, 1H); 8.04 (d, J=9.0 Hz, 2H); 7.0 (d, J=9.0 Hz, 2H); 6.75 (s, 1H); 3.99 (s, 3H): 3.86 (s, 3H).

Example 24

Prepared from T and purified as described for example 22 giving 30 mg (54%), yellow solid. ¹H NMR (300 MHz, CDCl₃): δ 8.48 (s, 1H), 7.55 (d, J=8.9 Hz, 2H), 7.09 (s, 2H), 6.85 (s, 1H), 6.81 (d, J=8.9 Hz, 2H), 4.00 (s, 3H), 3.86 (s, 3H), 3.78 (s, 3H), 3.69 (s, 6H).

Example 25

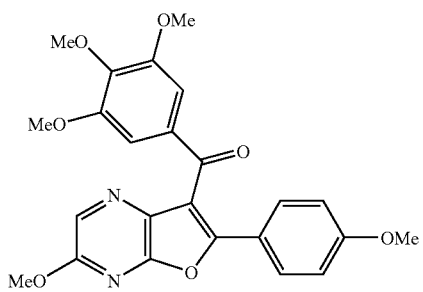

3-methoxy-6-(4-methoxyphenyl)-7-(3,4,5-trimethoxybenzoyl)furo[2,3-b]pyrazine

This compound was prepared according to the following reaction sequence:

1,6-Dimethoxypyrazine (V): A mixture of 1,6-dichloropiperazine U (3.9 g; 26 mmol) and freshly prepared sodium methoxide (62 mmol) in anhydrous methanol (50 ml) was refluxed overnight and the solvent was removed under reduced pressure. The residue was diluted to 100 ml with CH₂Cl₂ and the solution washed with water, brine and dried over anhydrous MgSO₄ and filtered off. The filtrate was evaporated under reduced pressure to give pure 1,6-dimethoxypiperazine V (3.6 g; 98%) as a colourless crystals. ¹HNMR (CDCl₃) 3.94 (s, 6H); 7.76 (s, 2H).

5-Bromo-1,6-dimethoxypyrazine (W): Prepared from V according to the procedure converting P into Q giving W in 48% yield, as a colourless crystals. ¹HNMR (CDCl₃) δ 7.57 (s, 1H); 4.01 (s, 3H); 3.93 (s, 3H).

2,6-Dimethoxy-5-(4-methoxyphenylethynyl)pyrazine (X): A mixture of 5-bromo-1,6-dimethoxypyrazine W (0.262 g; 1.2 mmol), 4-methoxyphenylacetylene (0.19 g; 1.44 Mmol), Cl₂Pd(PPh₃)₂ (0.07 g; 0.1 mmol) and CuI (2.6 mg; 0.014 mmol) in piperidine (8 ml) was stirred at room temperature for 12 h under N₂. To it saturated NH₄Cl (10 ml) was added and the resulting mixture was extracted with diethyl ether (3×15 ml). The organic phase was washed with brine and dried over anhydrous MgSO₄ and filtered off. The filtrate was evaporated under reduced pressure and the residue was purified by column chromatography (silica gel; CH₂Cl₂) to give pure title product as a colourless solid ¹HNMR (CDCl₃) δ 7.79 (s, 1H) 7.52 (d, J=8.82, 2H); 6.85 (d, J=8.82 Hz, 2H); 4.03 (s, 3H); 3.97 (s, 3H); 3.81 (s, 3H).

7-Iodo-3-methoxy-6-(4-methoxyphenyl)furo[2,3-b]pyrazine (Y): Prepared from X according to the procedure for converting S into T (above) giving Y in 27% yield, as a yellow crystals. ¹HNMR (CDCl₃) δ 8.22 (s, 1H). 8.15 (d, J=9.0 Hz, 2H); 7.02 (d, J=9.0 Hz, 2H); 4.04 (s, 3H); 3.87 (s, 3H).

Example 25

Prepared and purified as described for example 22 giving 12 mg (27%), yellow solid. ¹H NMR (300 MHz, CDCl₃) δ 8.21 (s, 1H), 7.74 (d, J=9.0 Hz, 2H), 7.23 (s, 2H), 6.88 (d, J=9.0 Hz, 2H), 3.90 (s, 3H), 3.88 (s, 3H), 3.81 (s, 3H), 3.74 (s, 6H).

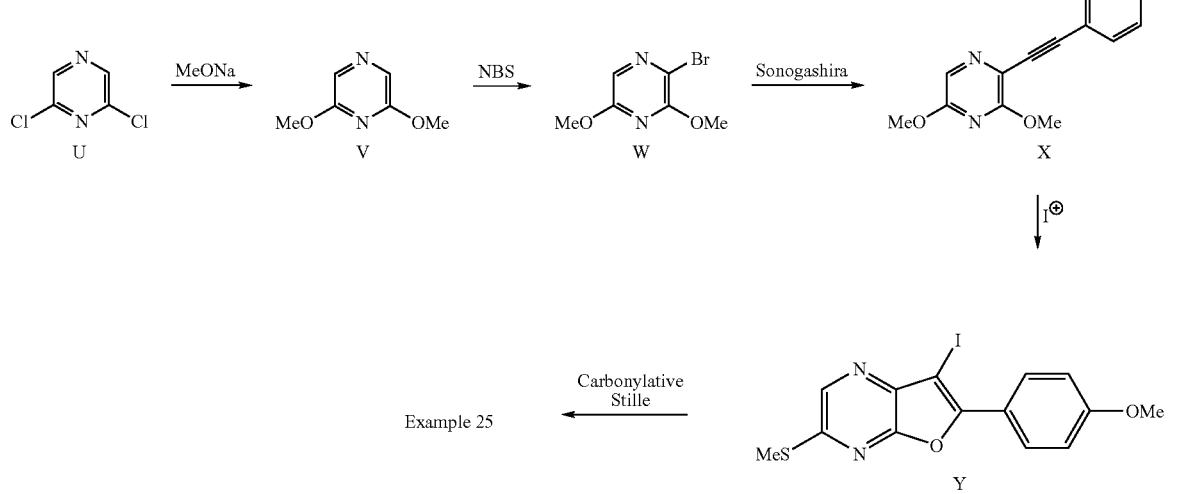

Example 26

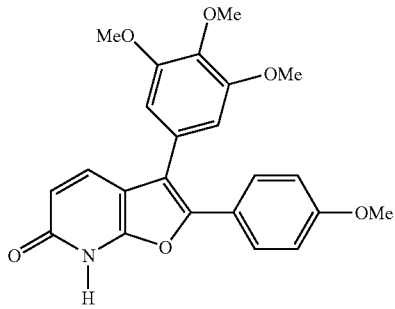

2-(4-Methoxyphenyl)-3-(3,4,5-trimethoxyphenyl)furo[2,3-b]pyridin-6-one

Chlorotrimethylsilane (40 µl, 0.31 mmol) was added to a mixture of example 21 (13.2 mg, 0.0313 mmol) and sodium iodide 5 mg (0.033 mmol) in anhydrous acetonitrile (2 ml). The resulting mixture was refluxed for 1 h under nitrogen atmosphere. After evaporation of solvent under reduced pressure the residue was dissolved in methanol (1 ml), evaporated to dryness under reduced pressure and purified by preparative thin layer chromatography (silica gel, hexane/ethyl acetate 1:1) to give 3.2 mg (25% yield) of pure product. $^1$HNMR (CDCl$_3$, 300 MHz) δ 7.80 (d, J=8.4 Hz, 1H). 7.15 (d, J=9.0 Hz, 2H); 6.84 (d, J=9.0 Hz, 2H); 6.76 (d, J=8.4 Hz, 1H); 6.67 (s, 2H); 3.93 (s, 3H); 3.81 (m, 10H, 3×OMe, NH).

Example 27

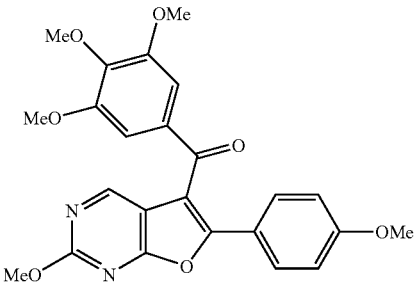

2-Methoxy-6-(4-methoxy-phenyl)-3-(3,4,5-trimethoxybenzoyl)-furo[2,3-d]pyrimidine This compound was prepared according to the following reaction sequence:

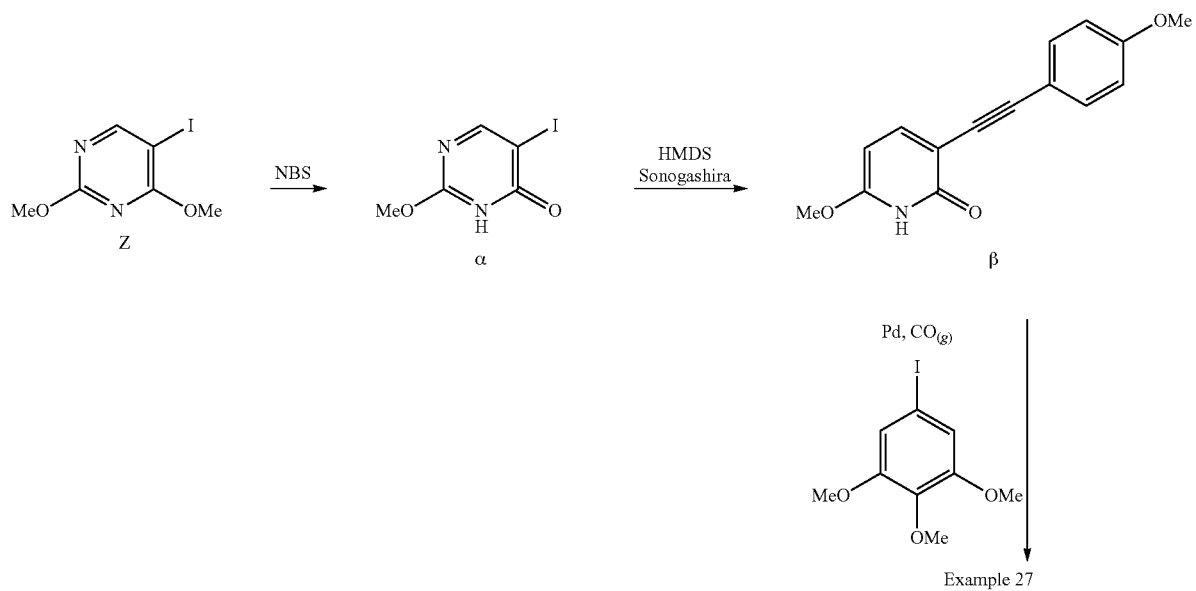

5-Iodo-2-methoxy-3H-4-pyrimidinone (α): 2,4-Dimethoxy-5-iodopyrimidine Z (2.54 g, 9.6 mmol) was added to 26 ml of 5N sodium hydroxide in 50% aqueous methanol and the resulting solution was refluxed overnight. The reaction mixture was evaporated to dryness under reduced pressure, diluted to 25 ml with water and neutralized to ph ~6 with 1N hydrochloric acid. The precipitate was filtered off, washed with water (2×10 ml), methanol (2×10 ml) and diethyl ether to give 0.55 g of pure product. The filtrate was concentrated under reduced pressure and kept overnight at 4° C. The crystals of the product were filtered off washed as above to give additional 0.3 g of pure product as a colorless crystals (total yield 0.85 g, 35%). $^1$HNMR (DMSO-d6, 300 MHz) δ 8.14 (s, 1H) 3.82 (s, 3H); 3.3 (broad s, 1H).

2-Methoxy-5-(4-methoxy-phenylethynyl)-3H-pyrimidin-4-one (β): A suspension of 0.2 g (0.794 mmol) of the above product in 1 ml of 1,1,1,3,3,3-hexamethyl disilazane (HMDS) was refluxed under nitrogen atmosphere until the reaction mixture became homogenous (~20 minutes). The excess of HMDS was removed under reduced pressure. To the residue 0.126 g (0.95 mmol) of 4-methoxyphenylethyne was added followed by the addition of 0.045 g (0.064 mmol) of dichlorobis(triphenylphosphine)palladium(II) and 0.007 g (0.037 mmol) of copper(I) iodide. The resulting mixture was dissolved in 8 ml of tetrahydrofuran/piperidine 1:1 mixture and stirred for 3 hours. The resulting mixture was diluted to 100 ml with ethyl acetate, washed with aqueous saturated ammonium chloride, dried over anhydrous magnesium sulfate to give 0.07 g (34% yield) of the title compound. $^1$HNMR (DMSO-d6, 300 MHz) δ 8.02 (s, 1H); 7.37 (d, J=9.0 Hz, 2H); 6.92 (d, J=9.0 Hz, 2H); 3.88 (s, 3H); 3.75 (s, 3H); 3.28 (broad s, 1H).

Example 27

A mixture of β (52 mg, 0.2 mmol), 3,4,5-trimethoxyiodobenzene (72 mg, 0.24 mmol) and anhydrous potassium carbonate (14 mg, 1.01 mmol) (dried at 130° C. under vacuum for 2 hours) and of dichlorobis(triphenylphosphine)palladium (9.0 mg, 0.013 mmol) in anhydrous dimethylsulfoxide (3 ml) was degassed in vacuo and saturated with carbon monoxide. The resulting mixture was vigorously stirred overnight at 100° C. under carbon monoxide atmosphere. After cooling down to room temperature, the mixture was diluted to 200 ml with ethyl acetate, washed with saturated aqueous ammonium chloride (2×50 ml) and dried over anhydrous magnesium sulfate. Evaporation of the solvent under reduced pressure gave 0.082 g of a mixture of Example 27, which was separated by fractional crystallization form ethyl acetate to give 0.012 g of pure 2-methoxy-6-(4-methoxy-phenyl)-5-(3,4,5-trimethoxy-phenyl)-furo[2,3-d]pyrimidine. The filtrate was evaporated to dryness under reduced pressure and the residue was recrystallized form the ethyl acetate/ethanol mixture to give pure Example 27 (20 mg, 22%). $^1$HNMR (CDCl3, 300 MHz) δ 8.79 (s, 1H) 7.57 (d, J=8.9 Hz, 2H); 7.07 (s, 2H); 6.82 (d, J=8.9 Hz, 2H); 4.1 (s, 3H); 3.87 (s, 3H); 3.79 (s, 3H); 3.68 (s, 6H).

Example 28

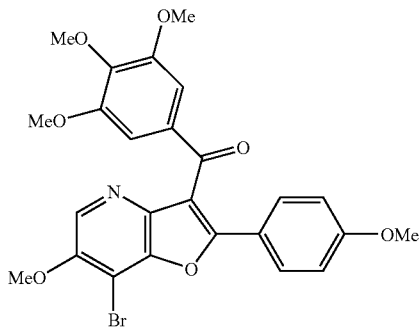 [SMILES: COc1ccc(-c2oc3c(Br)c(OC)cnc3c2C(=O)c2cc(OC)c(OC)c(OC)c2)cc1]

7-Bromo-6-methoxy-2-(4-methoxyphenyl)-3-(3,4,5-trimethoxybenzoyl)-furo[3,2-b]pyridine This material was prepared according to the following reaction sequence:

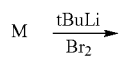

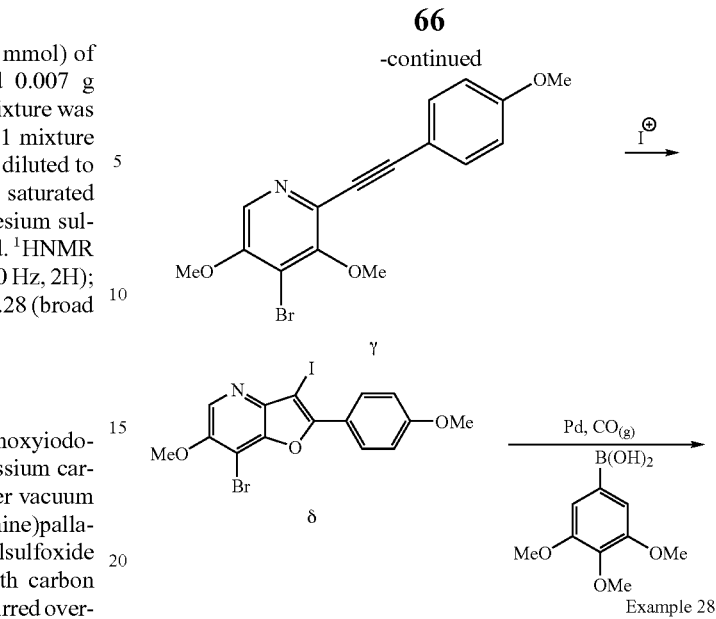

4-Bromo-3,5-dimethoxy-2-(4-methoxyphenylethynyl)pyridine (γ): To a solution of 3,5-dimethoxy-2-(4-methoxyphenylethynyl)pyridine M (120 mg, 0.446 mmol) in dry THF (2.5 ml) at −78° C. was added t-butyllithium (0.49 mmol, 0.30 ml of a 1.6M solution in pentane) and the reaction stirred for 10 minutes. After this time bromine (25 μL, 0.50 mmol) was added neat and the reaction was allowed to warm to room temperature and quenched by the addition of water (10 ml) and ethyl acetate (10 ml). The organic layer was washed with brine (10 ml), dried over MgSO4 and concentrated under reduced pressure. The crude residue was purified by flash chromatography (silica-gel, eluted with hexanes:EtOAc, 3:1) to afford the product as a white solid (45 mg, 29%). $^1$HNMR (300 MHz, CDCl3) δ 7.99 (s, 1H), 7.52 (d, J=8.7 Hz, 2H), 6.87 (d, J=8.7 Hz, 2H), 4.05 (s, 3H), 4.01 (s, 3H), 3.82 (s, 3H).

7-Bromo-3-iodo-6-methoxy-2-(4-methoxyphenyl)-furo[3,2-b]pyridine (δ): To a solution γ (160 mg, 0.46 mmol) in dry THF (5 ml) was added bispyridineiodonium tetrafluoroborate (210 mg, 0.55 mmol) and the reaction was refluxed for 45 minutes. After this time the solution was cooled and quenched with 10% Na2S2O3 (aq) (20 ml) and ethyl acetate (20 ml). The organic layer was washed with brine (15 ml), dried over MgSO4 and concentrated under reduced pressure. The crude residue was purified by flash chromatography (silica-gel, eluted sequentially with CH2Cl2: hexanes, 3:1 then CH2Cl2) to afford the product as a white solid (140 mg, 66%). $^1$HNMR (300 MHz, CDCl3) δ 8.26 (s, 1H), 8.18 (d, J=8.9 Hz, 2H), 7.03 (d, J=8.9 Hz, 2H), 4.05 (s, 3H), 3.88 (s, 3H).

Example 28

A mixture of 7-bromo-6-methoxy-2-(4-methoxyphenyl)-3-(3,4,5-trimethoxybenzoyl)-furo[3,2-b]pyridine (γ) (140 mg, 0.304 mmol), dry K2CO3 (s) (126 mg, 0.912 mmol), 3,4,5-trimethoxyphenylboronic acid (96 mg, 0.453 mmol) and Pd(Ph3P)4 (30 mg) in dry anisole (12 ml) was placed in a high pressure reaction vessel and charged with a carbon monoxide atmosphere (180 psi). The reaction vessel was heated to 90° C. for 72 hours. After this time all the solvent had evaporated so further quantities of the boronic acid (50 mg), K2CO3 (s) (100 mg), Pd(Ph3P)4 (20 mg) and dry anisole (12 ml) were added and the reaction continued for an additional 48 hours.

After cooling the crude mixture was diluted with CH₂Cl₂ and filtered through celite. The filtrate was concentrated onto silica-gel under reduced pressure and purified by flash chromatography (silica-gel, sequentially eluting with hexanes: CH₂Cl₂, 1:4 then CH₂Cl₂ then CH₂Cl₂: EtOAc, 9:1) to initially afford recovered starting material (45 mg, 32% recovery) and then the carbonylatively coupled product, which was further purified by recrystallisation from CH₂Cl₂: hexanes (14 mg, 9%). ¹HNMR (300 MHz, CDCl₃) δ 8.20 (s, 1H), 7.73 (d, J=8.9 Hz, 2H), 7.23 (s, 2H), 6.89 (d, J=8.9 Hz, 2H), 4.03 (s, 3H), 3.89 (s, 3H), 3.81 (s, 3H), 3.73 (s, 6H). MS (ES) m/z 528.1/530.1 (M+H⁺).

Example 29

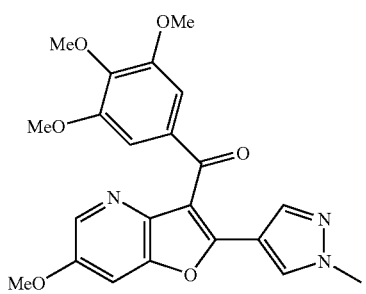 [SMILES: COc1cnc2c(C(=O)c3cc(OC)c(OC)c(OC)c3)c(-c3cnn(C)c3)oc2c1]

(6-Methoxy-2-(1-methyl-1H-pyrazol-4-yl)-3-(3,4,5-trimethoxybenzoyl)-furo[3,2-b]pyridine This material was prepared according to the following reaction sequence:

2-Bromo-3,5-dimethoxypyridine (ε): To a stirred solution of 3,5-dimethoxypyridine (780 mg, 5.6 mmol) in dry MeCN (24 ml) was added N-bromosuccinimide (1.0 g, 5.6 mmol) and the reaction was heated to reflux for 1 hour. After cooling, the solvent was removed under vacuum and the residue was triturated with diethyl ether to precipitate the succinimide by-product and filtered. The filtrate was concentrated onto silica-gel and the residue purified by flash chromatography (silica-gel, eluted with hexanes:EtOAc, 3:1) to afford the product as a white solid (860 mg, 70%). ¹H-NMR (300 MHz, CDCl₃) δ 7.67 (d, J=2.5 Hz, 1H), 6.71 (d, J=2.5 Hz, 1H), 3.87 (s, 3H), 3.85 (s, 3H).

3,5-Dimethoxy-2-(1-methyl-1H-pyrazol-4-ethynyl)-pyridine (φ): To a stirred solution of 2-bromo-3,5-dimethoxypyridine (ε) (218 mg, 1.0 mmol) and 4-ethynyl-1-methyl-1H-pyrazole (1.1 mmol) in dry MeCN (4 ml) and NEt₃ (1 ml) was added Pd(Ph₃P)₂Cl₂ (21 mg, 3 mol %) and the reaction vessel was evacuated and backfilled with nitrogen three times. Copper (I) iodide (15 mg, 8 mol %) was added and the reaction mixture rapidly became dark. Stirring was continued overnight and the crude mixture was concentrated directly onto silica-gel under reduced pressure and purified by flash chromatography (silica-gel, eluted sequentially with EtOAc:hexanes, 1:1, 3:1, 1:0) to give the product as a tan solid (205 mg, 84%). ¹H-NMR (300 MHz, CDCl₃) δ 7.89 (d, J=1.6 Hz, 1H), 7.66 (s, 1H), 7.57 (s, 1H), 6.72 (d, J=1.6 Hz, 1H), 3.88 (s, 9H).

3-Iodo-6-methoxy-2-(1-methyl-1H-pyrazol-4-yl)-furo[3,2-b]pyridine (λ): To a stirred solution of 3,5-dimethoxy-2-(1-methyl-1H-pyrazol-4-ethynyl)-pyridine (φ) (60 mg, 0.247 mmol) in dry THF (2 ml) was added bispyridine iodonium tetrafluoroborate (115 mg, 0.31 mmol) and the reaction heated to reflux for 1 hour. After cooling, the reaction was diluted with EtOAc and quenched with 10% Na₂S₂O₃ ₍aq₎. The organic layer was washed with brine, dried over MgSO₄ and concentrated onto silica-gel under reduced pressure. The solid residue was purified by flash chromatography (silica-gel, eluted with EtOAc: hexanes, 1:1) to give the product as a white solid (62 mg, 71%). ¹H-NMR (300 MHz, CDCl₃) δ 8.30 (d, J=2.1 Hz, 1H), 8.16 (s, 2H), 7.23 (d, J=2.1 Hz, 1H), 3.98 (s, 3H), 3.89 (s, 3H).

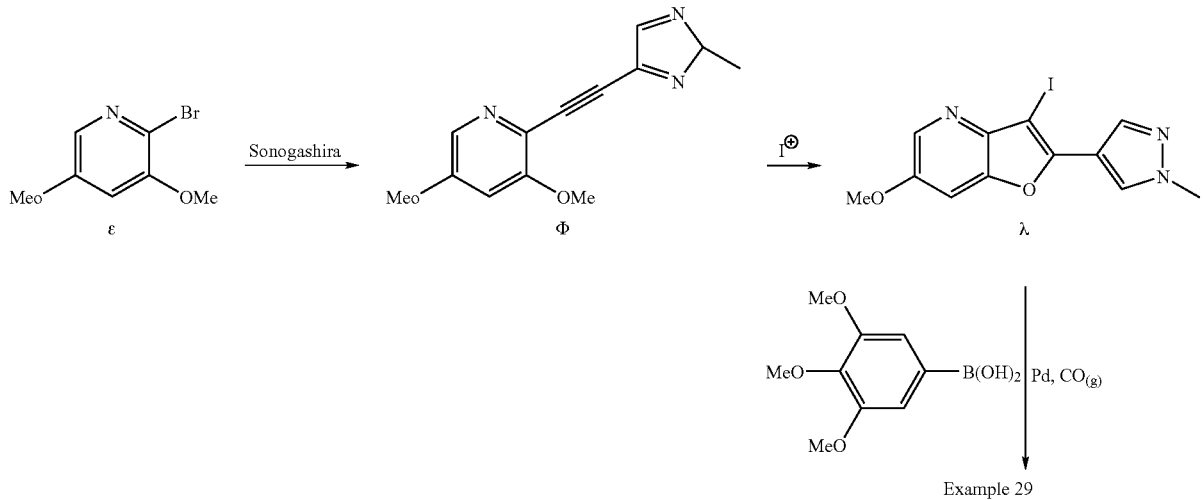

Example 29

A suspension of 3-iodo-6-methoxy-2-(1-methyl-1H-pyrazol-4-yl)furo[3,2-b]pyridine (λ) (57.6 mg, 0.162 mmol), 3,4,5-trimethoxyphenyl boronic acid (0.058 g, 0.27 mmol), dry K₂CO₃ (0.075 g, 0.55 mmol) and Pd(PPh₃)₂Cl₂ (0.016 g, 0.014 mmol) in anhydrous anisole (8 ml) was placed in Parr mini bench top reactor (series 4561, 300 ml). The reactor was degassed under reduced pressure and flashed with dry N₂ than flashed three times with CO by pressurizing the reactor up to 180 psi and depressurizing. Finally, the reactor was pressurized to 180 psi and stirred at 85° C. (the temperature of external oil bath) for ~30 h. The reactor was cooled down to room temperature and the reaction mixture was diluted to with CH$_2$Cl$_2$ (20 ml) and filtered through celite. The celite pad was washed with fresh portion of CH$_2$Cl$_2$ (3×20 ml) and combined filtrates were evaporated to dryness under reduced pressure. The residue was purified by flash column chromatography (silica-gel, eluted with CH$_2$Cl$_2$/ethyl acetate 9:1) giving the product of Example xx as a creamy solid (0.043 g, 78%) as a colorless solid. $^1$H NMR (300 MHz, CDCl$_3$) δ 3.78 (s, 6H), 3.9 (s, 3H), 3.92 (s 3H), 3.94 (s, 3H), 7.25 (s, 2H), 7.33 (d, J=2.5 Hz, 1H), 8.05 (s, 1H), 8.24 (d, J=2.5 Hz, 1H), 8.51 (s, 1H).

Example 30

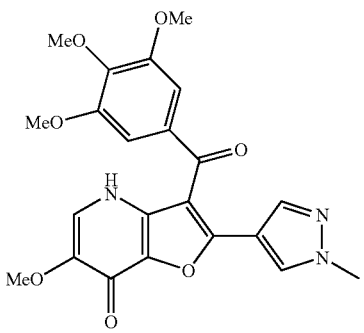 [SMILES: COc1cc(C(=O)c2c(-c3cnn(C)c3)oc3c(=O)c(OC)c[nH]c23)cc(OC)c1OC]

6-Methoxy-2-(1-methyl-1H-pyrazol-4-yl)-3-(3,4,5-trimethoxybenzoyl)-4H-furo[3,2-b]pyridin-7-one This material was prepared according to the following reaction sequence:

reaction was re-cooled and treated with bromine (1.5 ml, 29.1 mmol) and again allowed to warm to room temperature. After stirring for 10 minutes the solution became homogeneous and was quenched with 10% Na$_2$S$_2$O$_3$ $_{(aq)}$ and extracted with EtOAc. The organic layer was washed with brine, dried over MgSO$_4$ and concentrated onto silica-gel under reduced pressure. The solid residue was purified by flash chromatography (silica-gel, eluted sequentially with hexanes:EtOAc, 2:1, 1:1, 1:2) to give the product as a white solid (2.4 g, 57%). $^1$H-NMR (300 MHz, CDCl$_3$) δ 7.95 (s, 2H), 3.99 (s, 6H).

3,5-Dimethoxy-4-(4-methoxy-benzyloxy)-pyridine (v): To an ice-cooled suspension of sodium hydride (60% dispersion in mineral oil, 650 mg, 16.3 mmol) in dry DMF (10 ml) was added 4-methoxybenzyl alcohol (2.24 g, 16.3 mmol) drop-wise via syringe. Vigorous evolution of hydrogen was observed and the reaction was allowed to warm to room temperature and stirred for 15 minutes. 4-Bromo-3,5-dimethoxypyridine (1.17 g, 5.41 mmol) was added and the reaction heated to 90° C. overnight. After cooling, only trace starting material could be detected by TLC analysis and the reaction was quenched with water and extracted with EtOAc. The organic layer was washed with water 3 times then brine, dried over MgSO$_4$ and concentrated onto silica-gel under reduced pressure. The solid residue was purified by flash chromatography (silica-gel, eluted sequentially with EtOAc: hexanes, 2:1, 1:0) to give the product as a tan solid (865 mg, 58%). $^1$H—NMR (300 MHz, CDCl$_3$) δ 7.96 (s, 2H), 7.33 (d, J=8.5 Hz, 2H), 6.84 (d, J=8.5 Hz, 2H), 5.11 (s, 2H), 3.89 (s, 6H), 3.78 (s, 3H). MS (ES$^+$) m/z 276.1 (M+H$^+$).

2-Iodo-3,5-dimethoxy-4-(4-methoxy-benzyloxy)-pyridine (π): To a solution of 3,5-dimethoxy-4-(4-methoxy-benzyloxy)-pyridine (120 mg, 0.436 mmol) in dry THF (3 ml) at −78° C. was added t-butyllithium (0.48 mmol, 1.7 M solution in pentane) and the resulting orange mixture was stirred at low temperature for 10 minutes. A solution of iodine (166 mg, 0.654 mmol) in dry THF (2 ml) was added drop-wise and the reaction allowed to warm to room temperature and stir for 15

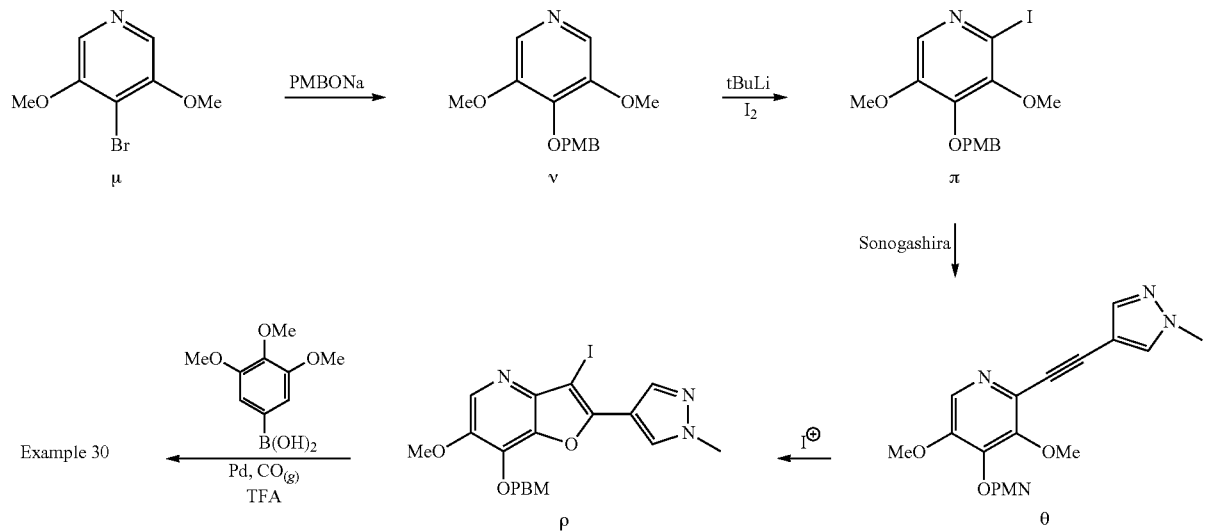

4-Bromo-3,5-dimethoxy-pyridine (μ): To a stirred solution of 3,5-dimethoxypyridine (2.7 g, 19.4 mmol) in dry THF at −78° C. was added n-butyllithium (23.3 mmol, 2 M solution in cyclohexanes). During this addition a precipitate formed and the reaction was allowed to warm to room temperature for 5 minutes. The precipitate separated into an oily phase and the minutes, then quenched with 10% Na$_2$S$_2$O$_3$ $_{(aq)}$ and extracted with EtOAc. The organic layer was washed with brine, dried over MgSO$_4$ and concentrated onto silica-gel under reduced pressure. The solid residue was purified by flash chromatography (silica-gel, eluted with hexanes:EtOAc, 4:1) to give the product as a tan solid (100 mg, 57%). $^1$H-NMR (300 MHz, CDCl$_3$) δ 7.83 (s, 1H), 7.33 (d, J=8.6 Hz, 2H), 6.86 (d, J=8.6 Hz, 2H), 5.11 (s, 2H), 3.88 (s, 3H), 3.85 (s, 3H), 3.79 (s, 3H).

3,5-Dimethoxy-4-(4-methoxy-benzyloxy)-2-(1-methyl-1H-pyrazol-4-ylethynyl)-pyridine (θ): To a stirred solution of 2-iodo-3,5-dimethoxy-4-(4-methoxy-benzyloxy)-pyridine (95 mg, 0.237 mmol) and 4-ethynyl-1-methyl-1H-pyrazole (30 mg, 0.283 mmol) in dry MeCN (1.5 ml) and NEt$_3$ (0.5 ml) was added Pd(Ph$_3$P)$_2$Cl$_2$ (12 mg, 7 mol %) and the reaction vessel was evacuated and backfilled with nitrogen three times. Copper (I) iodide (5 mg, 11 mol %) was added and the reaction mixture immediately became dark. Stirring was continued for 0.5 hours then the crude mixture was concentrated directly onto silica-gel under reduced pressure and the solid residue was purified by flash chromatography (silica-gel, eluted sequentially with EtOAc:hexanes, 2:1, 3:1, 1:0) to give the product as a white solid (85 mg, 95%). $^1$H—NMR (300 MHz, CDCl$_3$) δ 7.98 (s, 1H), 7.66 (s, 1H), 7.57 (s, 1H), 7.34 (d, J=8.6 Hz, 2H), 6.86 (d, J=2H), 5.13 (s, 2H), 3.93 (s, 3H), 3.91 (s, 3H), 3.89 (s, 3H), 3.78 (s, 3H).

3-Iodo-6-methoxy-7-(4-methoxy-benzyloxy)-2-(1-methyl-1H-pyrazol-4-yl)-furo[3,2-b]pyridine (ρ): To a stirred solution of 3,5-dimethoxy-4-(4-methoxy-benzyloxy)-2-(1-methyl-1H-pyrazol-4-ylethynyl)pyridine (80 mg, 0.21 mmol) in dry THF (2 ml) was added bispyridine iodonium tetrafluoroborate (94 mg, 0.25 mmol) and the reaction was refluxed for 0.5 hours. After cooling, the reaction was quenched with 10% Na$_2$S$_2$O$_3$ $_{(aq)}$ and extracted with EtOAc. The organic layer was washed with brine, dried over MgSO$_4$ and concentrated onto silica-gel under reduced pressure. The solid residue was purified by flash chromatography (silica-gel, eluted with EtOAc:hexanes, 3:2) to give the product as a white solid (65 mg, 63%). $^1$H—NMR (300 MHz, CDCl$_3$) δ 8.23 (s, 1H), 8.16 (s, 1H), 8.15 (s, 1H), 7.38 (d, J=8.6 Hz, 2H), 6.86 (d, J=8.6 Hz, 2H), 5.60 (s, 2H), 3.99 (s, 3H), 3.93 (s, 3H), 3.77 (s, 3H).

Example 30

A mixture of 3-iodo-6-methoxy-7-(4-methoxy-benzyloxy)-2-(1-methyl-1H-pyrazol-4-yl)-furo[3,2-b]pyridine (250 mg, 0.509 mmol), dry K$_2$CO$_3$ $_{(s)}$ (211 mg, 1.53 mmol), 3,4,5-trimethoxyphenyl boronic acid (215 mg, 1.01 mmol) and Pd(Ph$_3$P)$_4$ (45 mg) in dry anisole (18 ml) was placed in a high pressure reaction vessel and charged with a carbon monoxide atmosphere (180 psi). The reaction vessel was heated to 90° C. for 48 hours. After this time all the solvent had evaporated and the crude residue was treated with CH$_2$Cl$_2$ and filtered through celite. The filtrate was concentrated onto silica-gel under reduced pressure and purified by flash chromatography (silica-gel, eluted with EtOAc: CH$_2$Cl$_2$, 2:3) to give a 1:1 mixture of the starting 3-iodo compound and the desired carbonylatively coupled product (205 mg). A portion of this mixture (50 mg) was dissolved in trifluoroacetic acid (1.5 ml) and anisole (25 μL). The solution obtained an iodine colour that gradually faded and after 1 hour TLC analysis revealed complete consumption of the starting materials. The crude reaction mixture was concentrated under reduced pressure and the residue purified by flash chromatography (silica-gel, eluted sequentially with CH$_2$Cl$_2$: EtOAc:MeOH, 2:1:0, 60:25:5) to give the product as a white solid (14 mg, 26%). $^1$H—NMR (300 MHz, CDCl$_3$) δ 10.65 (br s, 1H), 7.56 (s, 1H), 7.46 (s, 1H), 7.38 (s, 1H), 6.94 (s, 2H), 3.86 (s, 3H), 3.81 (s, 3H), 3.79 (s, 3H), 3.66 (s, 6H). MS (ES$^+$) m/z 440.2 (M+H$^+$).

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

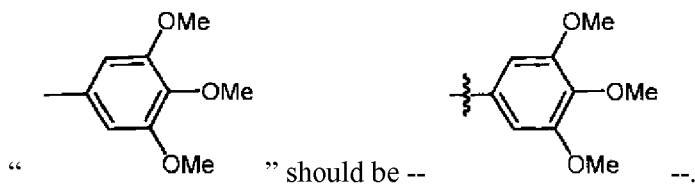

The invention claimed is:
1. A compound of formula:

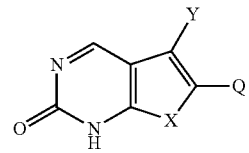

or a salt thereof, wherein;
X represents O;
Y represents a group of formula (i) or (ii);

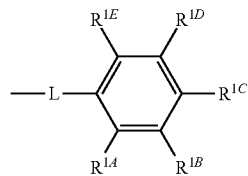

(i)

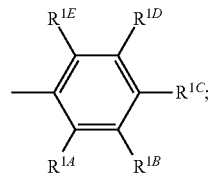

(ii)

wherein each one of R$^{1A}$, R$^{1B}$, R$^{1C}$, R$^{1D}$, and R$^{1E}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted , thioacyloxy; or any of $R^{1A}$ and $R^{1B}$, $R^{1B}$ and $R^{1C}$, $R^{1C}$ and $R^{1D}$, and $R^{1D}$ and $R^{1E}$, together form an optionally substituted aryl, optionally substituted heterocyclyl, optionally substituted heteroaryl, optionally substituted cycloalkyl, or optionally substituted cycloalkenyl;

L represents C=O, O, S, SO, $SO_2$, Se, SeO, $SeO_2$, C=NZ', or NR' where Z' is H, optionally substituted alkyl, optionally substituted aryl or optionally substituted amino, and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl; and Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl; and wherein Y and Q do not represent the same group.

2. A compound according to claim 1 or a salt thereof wherein Y represents a group of formula (i) where L is a carbonyl group (C=O) or a group of formula (ii).

3. A compound according to claim 1 or a salt thereof wherein $R^{1A}$ and $R^{1E}$ represents H.

4. A compound according to claim 3 or a salt thereof wherein furthermore $R^{1C}$ represents H, halogen, or an alkoxy group and $R^{1D}$ and $R^{1B}$ independently represent an alkoxy group.

5. A compound according to claim 4 or a salt thereof wherein $R^{1D}$, $R^{1C}$ and $R^{1B}$ represent an alkoxy group.

6. A compound according to claim 5 or a salt thereof wherein $R^{1A}$ and $R^{1E}$ represent H and $R^{1D}$, $R^{1C}$ and $R^{1B}$ represent methoxy.

7. A compound according to formula (Ic) or a salt thereof:

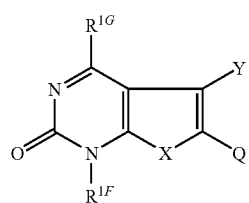

(Ic)

wherein;
X represents O;
$R^{1F}$ represents hydrogen, lower alkyl, lower alkylaryl, or optionally substituted phenyl;
$R^{1G}$ represents hydrogen, lower alkyl, lower alkoxy, lower alkylaryl, or optionally substituted phenyl;
Y represents a group of formula (i)(b) or (ii)(a);

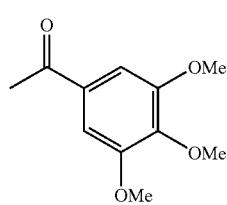

(i)(b)

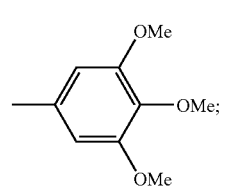

(ii)(a)

Q represents H, CN, halogen, trialkylsilyl, optionally substituted alkyl, optionally substituted alkenyl, optionally substituted alkynyl, optionally substituted aryl, optionally substituted heteroaryl, optionally substituted heterocyclyl, optionally substituted cycloalkyl, optionally substituted cycloalkenyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl; and wherein Y and Q do not represent the same group.

8. A compound according to claim 7 or a salt thereof wherein $R^{1F}$ is hydrogen or lower alkyl and $R^{1G}$ is hydrogen.

9. A compound according to claim 7 or a salt thereof wherein Q represents an optionally substituted phenyl group or an optionally substituted heteroaryl group.

10. A compound according to claim 7 or a salt thereof wherein Q represents indolyl, 1-methyl-indolyl, furanyl, pyrazolyl, or pyridinyl.

11. A compound selected from the group consisting of:
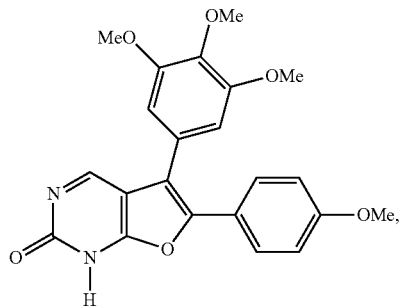
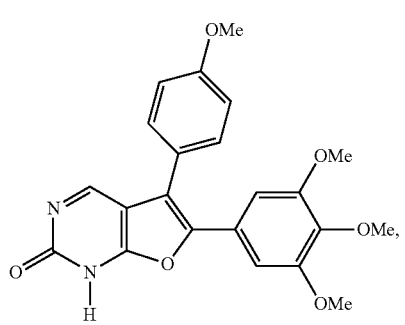
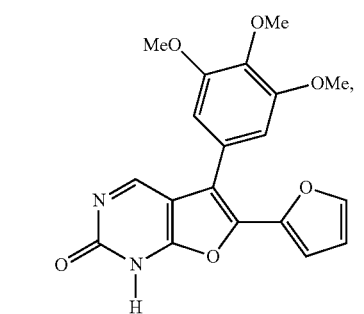
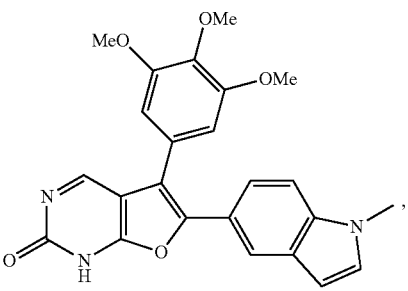
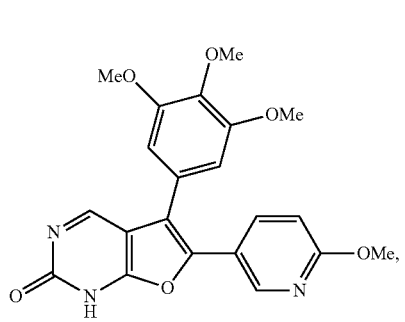
-continued
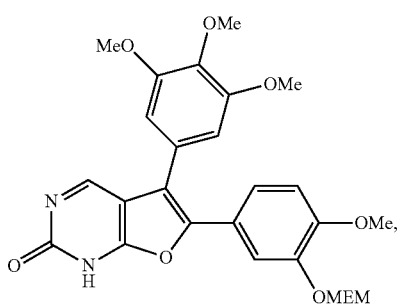
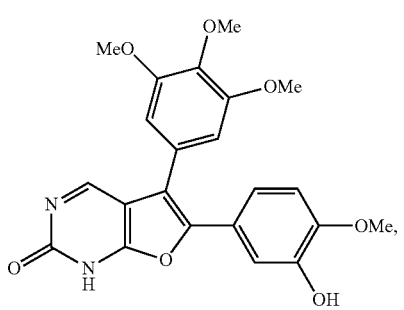
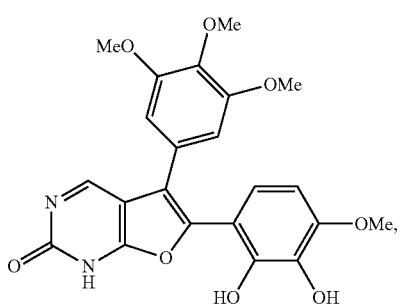
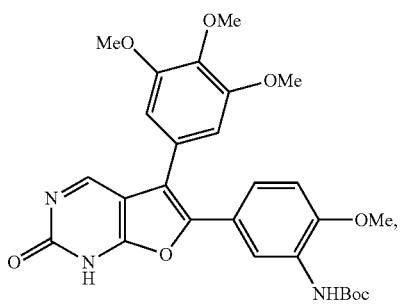
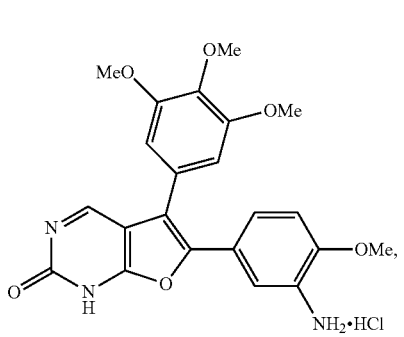

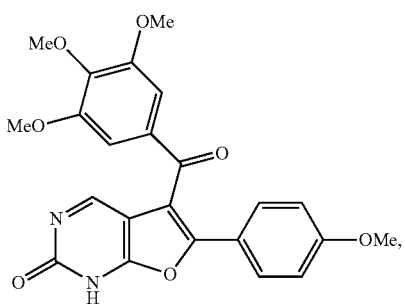

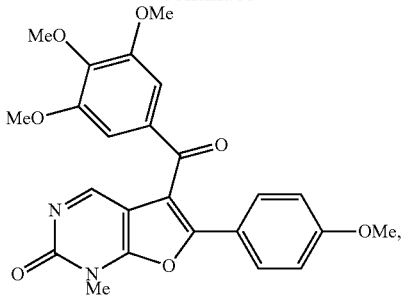

or a salt thereof.

12. A pharmaceutical composition comprising a compound according to claim 1 or a salt thereof together with a pharmaceutically acceptable additive.

13. A pharmaceutical composition comprising a compound according to claim 7 or a salt thereof together with a pharmaceutically acceptable additive.

14. A pharmaceutical composition comprising a compound according to claim 11 or a salt thereof together with a pharmaceutically acceptable additive.

15. A compound according to claim 1 or a salt thereof wherein Q represents an optionally substituted phenyl group or an optionally substituted heteroaryl group.

16. A compound according to claim 1 or a salt thereof wherein Q represents indolyl, 1-methyl-indolyl, furanyl, pyrazolyl, or pyridinyl.

* * * * *

UNITED STATES PATENT AND TRADEMARK OFFICE
CERTIFICATE OF CORRECTION

PATENT NO. : 8,466,163 B2
APPLICATION NO. : 12/448146
DATED : June 18, 2013
INVENTOR(S) : Bernard Luke Flynn et al.

It is certified that error appears in the above-identified patent and that said Letters Patent is hereby corrected as shown below:

In the Claims:

In claim 1, column 72, line 40, the formula:

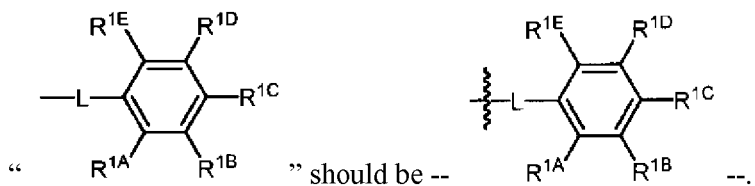

In claim 1, column 72, line 45, the formula:

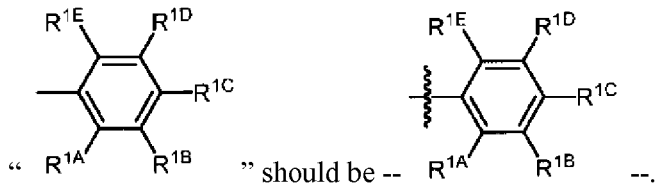

In claim 7, column 74, line 25, the formula:

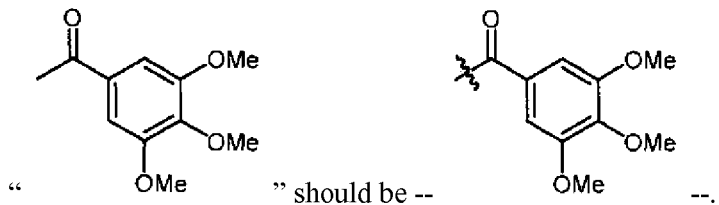

Signed and Sealed this
Fifteenth Day of October, 2013

Teresa Stanek Rea
*Deputy Director of the United States Patent and Trademark Office*

CERTIFICATE OF CORRECTION (continued)
U.S. Pat. No. 8,466,163 B2

In claim 7, column 74, line 35, the formula: